United States Patent
Fan et al.

(10) Patent No.: US 11,542,546 B2
(45) Date of Patent: *Jan. 3, 2023

(54) SYSTEMS AND METHODS FOR GENERATION OF EMULSIONS WITH SUITABLE CLARITY WITH APPLICATIONS OF USE

(71) Applicant: Enumerix, Inc., Palo Alto, CA (US)

(72) Inventors: Hei Mun Christina Fan, Palo Alto, CA (US); Eleen Yee Lam Shum, San Carlos, CA (US); Janice Hoiyi Lai, Mountain View, CA (US); Stephen P. A. Fodor, Palo Alto, CA (US)

(73) Assignee: Enumerix, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/673,598

(22) Filed: Feb. 16, 2022

(65) Prior Publication Data

US 2022/0170085 A1 Jun. 2, 2022

Related U.S. Application Data

(63) Continuation of application No. 17/561,608, filed on Dec. 23, 2021, which is a continuation of application No. 17/230,907, filed on Apr. 14, 2021, now Pat. No. 11,242,558.

(60) Provisional application No. 63/010,490, filed on Apr. 15, 2020.

(51) Int. Cl.
*C12Q 1/6851* (2018.01)
*C12Q 1/686* (2018.01)
*B01L 3/00* (2006.01)
*G01N 1/38* (2006.01)

(52) U.S. Cl.
CPC .......... *C12Q 1/6851* (2013.01); *B01L 3/5023* (2013.01); *C12Q 1/686* (2013.01); *G01N 1/38* (2013.01)

(58) Field of Classification Search
CPC .................. C12Q 1/6851; C12Q 1/686; C12Q 2563/159; B01L 3/5023; G01N 1/38
See application file for complete search history.

(56) References Cited

U.S. PATENT DOCUMENTS

| | | | |
|---|---|---|---|
| 5,216,033 A | 6/1993 | Pereira et al. | |
| 5,707,613 A | 1/1998 | Hill | |
| 5,753,241 A | 5/1998 | Ribier et al. | |
| 6,120,778 A | 9/2000 | Simonnet | |
| 6,121,055 A | 9/2000 | Hargreaves | |
| 6,379,682 B1 | 4/2002 | Tchinnis et al. | |
| 7,041,481 B2 * | 5/2006 | Anderson | C12Q 1/6844 435/287.2 |
| 8,871,444 B2 | 10/2014 | Griffiths et al. | |
| 8,889,093 B2 | 11/2014 | Malhotra et al. | |
| 9,012,390 B2 | 4/2015 | Holtze et al. | |
| 9,029,083 B2 | 5/2015 | Griffiths et al. | |
| 9,039,273 B2 | 5/2015 | Weitz et al. | |
| 9,074,242 B2 * | 7/2015 | Larson | C12Q 1/6816 |
| 9,127,310 B2 | 9/2015 | Larson et al. | |
| 9,410,151 B2 | 8/2016 | Link et al. | |
| 9,446,360 B2 | 9/2016 | Mazutis | |
| 9,562,837 B2 | 2/2017 | Link | |
| 9,610,239 B2 | 4/2017 | Feng et al. | |
| 9,788,564 B2 | 10/2017 | Bromley | |
| 10,537,503 B2 | 1/2020 | Lei et al. | |
| 10,619,192 B2 | 4/2020 | Chiu et al. | |
| 11,242,558 B2 * | 2/2022 | Fan | B01F 23/451 |
| 2006/0128883 A1 | 6/2006 | Garrison et al. | |
| 2008/0182910 A1 | 7/2008 | Qiu et al. | |
| 2009/0239308 A1 * | 9/2009 | Dube | C12Q 1/6837 435/288.7 |
| 2012/0322058 A1 * | 12/2012 | Regan | C12Q 1/6806 435/6.12 |
| 2018/0092847 A1 | 4/2018 | Schutt et al. | |
| 2018/0136114 A1 | 5/2018 | Delattre et al. | |
| 2019/0255531 A1 | 8/2019 | Hindson et al. | |
| 2019/0358625 A1 | 11/2019 | Huang et al. | |
| 2020/0037638 A1 | 2/2020 | Faraci et al. | |

* cited by examiner

FOREIGN PATENT DOCUMENTS

WO WO-2009149449 A1 12/2009

OTHER PUBLICATIONS

Huang et al., Centrifugal micro-channel array droplet generation for highly parallel digital PCR. Lap on a Chip 17(2): 235-240 (2017).

*Primary Examiner* — David C Thomas
(74) *Attorney, Agent, or Firm* — Wilson Sonsini Goodrich Rosati

(57) ABSTRACT

The inventions cover systems and methods for generation of emulsions having suitable clarity without requiring refractive index matching between emulsion components. Systems can include: a substrate including a set of openings; a reservoir facing the substrate at a first side and containing a sample fluid configured for droplet formation upon interacting with the set of openings of the substrate; and a collecting container facing the substrate at a second side and containing a set of fluid layers configured with a density gradient and suitable immiscibility characteristics. One or more components of the system(s) can support methods for emulsion generation, in relation to enabling interactions between multiple continuous phases and a dispersed droplet phase to generate clear emulsions. Applications of the inventions(s) can include performance of droplet-based digital PCR in an improved manner (e.g., without requiring implementation of correction factors based upon Poisson statistics).

21 Claims, 15 Drawing Sheets

Method 300

generating a set of droplets from a sample fluid 310

generating an emulsion upon processing the set of droplets with a set of fluid layers 320, where each droplet of the disperse phase of the emulsion includes a thin film shell derived from at least one of the set of fluid layers, and wherein the emulsion has clarity above a threshold level without RI matching of components of the emulsion

FIGURE 6A

Method 300'

generating a set of droplets as a dispersed phase with a first continuous phase, as an early stage emulsion having clarity below a threshold level of clarity 310'

generating an emulsion (e.g., later stage emulsion having clarity above a threshold level of clarity) upon processing the early stage emulsion with at least a second continuous phase 320'

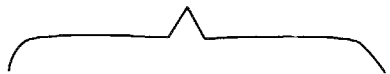

combining the second continuous phase with the early stage emulsion in a collecting container 322'

applying a force to the collecting container with the early stage emulsion and the second continuous phase to generate the later stage emulsion 323'

FIGURE 6C

Method 400'

generating a set of droplets from a sample fluid 410'

↓ generating an emulsion upon processing the set of droplets with a set of fluid layers 420'

↓ inducing one or more reactions upon processing the emulsion with a set of operations 430'

↓ detecting signals emitted from a subset of droplets containing target material from the sample fluid 440'

↓ performing a quantification operation with the subset of droplets 450'

FIGURE 7D

SYSTEMS AND METHODS FOR GENERATION OF EMULSIONS WITH SUITABLE CLARITY WITH APPLICATIONS OF USE

CROSS-REFERENCE TO RELATED APPLICATIONS

This application is a continuation of U.S. application Ser. No. 17/561,608, filed Dec. 23, 2021, which is a continuation of U.S. application Ser. No. 17/230,907, filed Apr. 14, 2021, now U.S. Pat. No. 11,242,558, issued Feb. 8, 2022, which claims the benefit of U.S. Provisional Application No. 63/010,490, filed Apr. 15, 2020, each of which is incorporated in its entirety herein by this reference.

TECHNICAL FIELD

This invention relates generally to fields related to sample processing, and more specifically to a new and useful system and method for generation of an emulsion with suitable clarity in fields related to sample processing.

BACKGROUND

An emulsion is composed of droplets of a first fluid (i.e., dispersed phase) in a second fluid (i.e., continuous phase) that is immiscible with the first fluid. Emulsions are typically cloudy due to scattering of light at surfaces of the droplets. Clarity of emulsions can be improved by aligning the refractive indices of the immiscible phases, thereby mitigating light scattering effects. Clarity of emulsions can also be improved by forming microemulsions or nanoemulsions, in which the characteristic droplet size is less than the wavelength(s) of light being used to irradiate the emulsion (e.g., less than 100 nm).

In biotechnology applications (e.g., cell-related applications, nucleic acid-derived analyses, protein analyses, etc.), however, useful droplet sizes are typically greater than 1 micron in diameter. In order to generate emulsions with suitable clarity, one has to match the refractive indices of the emulsion fluid components (e.g., of the dispersed phase and the continuous phase). However, this approach requires small tolerances in relation to matching of refractive indices. Furthermore, such an approach is extremely sensitive to user error. For instance, for compositions where the refractive indices are tuned by addition of compounds, minor pipetting errors can cause the refractive index of the final mixture to fall outside of a suitable range. Refractive indices also change with temperature, and the degree of change can be different for different types of fluid. Thus, there are also typically finite temperature ranges in which an emulsion remains clear, which may not be appropriate for applications requiring modifications to the temperature of the emulsion.

Thus, there is a need in the field of sample processing to create a new and useful system and method for generation of an emulsion having suitable clarity.

BRIEF DESCRIPTION OF THE FIGURES

FIG. 3A depicts submersion of a droplet-generating component in a liquid layer, and FIG. 3B depicts separation of the droplet-generating component from the liquid layer by a gas.

FIG. 4A depicts a water-in-oil-in-water emulsion and FIG. 4B depicts an oil-in-water-in-oil emulsion.

FIG. 6A depicts a flowchart of a first embodiment of a method for generating an emulsion.

FIG. 6C depicts a flowchart of a second embodiment of a method for generating an emulsion.

FIG. 7D depicts a flow chart of a variation of a method for performing droplet digital PCR.

DESCRIPTION OF THE PREFERRED EMBODIMENTS

Figure 1A:
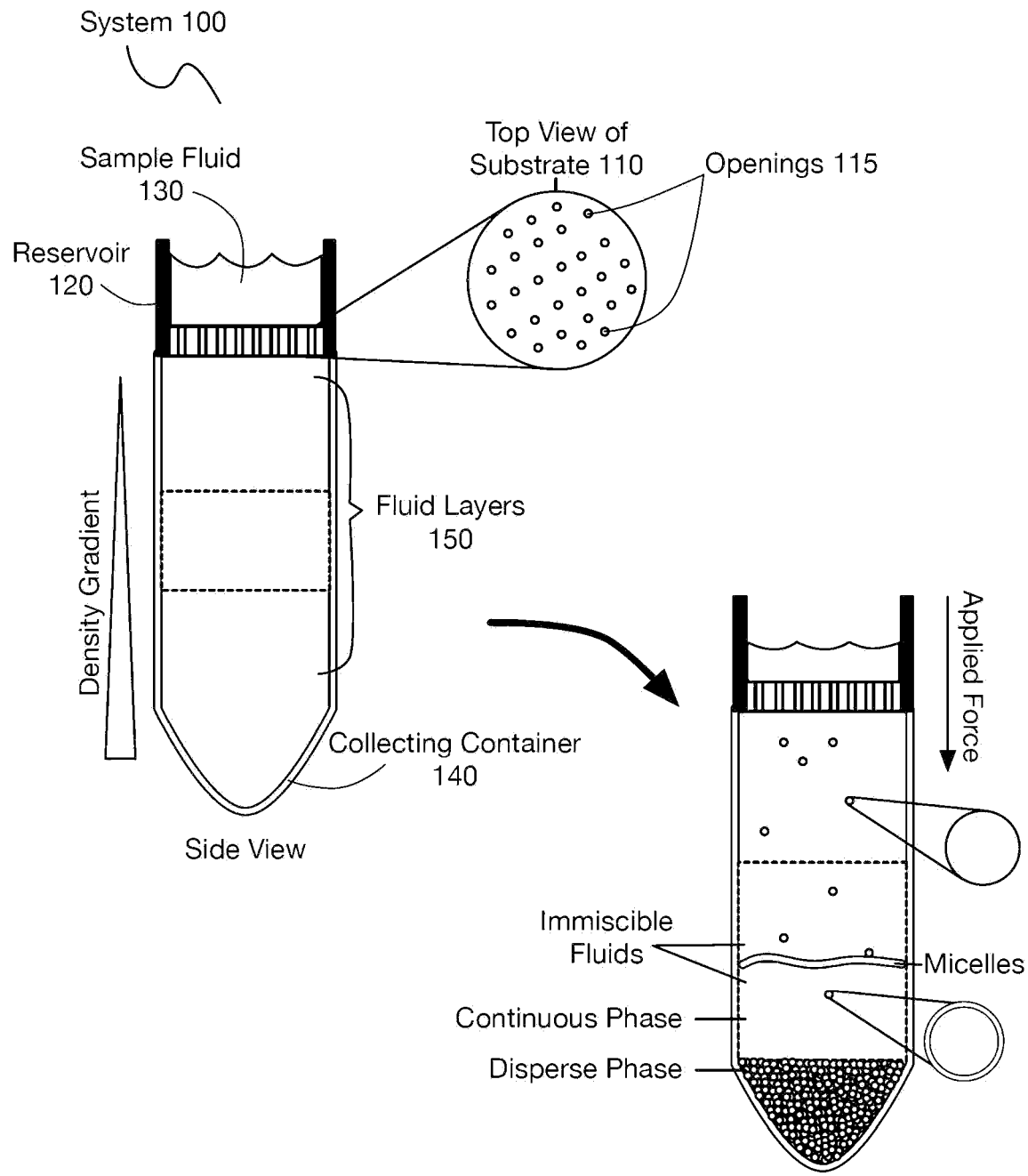
FIG. 1A depicts an embodiment of a system for generating an emulsion.

The following description of the preferred embodiments of the invention is not intended to limit the invention to these preferred embodiments, but rather to enable any person skilled in the art to make and use this invention.

1. Benefits

The inventions associated with the system and method can confer several benefits over conventional systems and methods, and such inventions are further implemented into many practical applications across various disciplines.

The invention(s) can provide methods and systems for forming clear emulsions with droplet sizes greater than wavelengths of light used to interrogate the emulsions for various applications, without requiring matching of the refractive indices of emulsion components (e.g., a dispersed phase and a continuous phase). Such invention(s) enable robust formation of emulsions having suitable clarity, with processes that are less subject to manual error (e.g., pipetting error). In particular, the invention(s) create emulsions with droplets having continuous fluid layers that are much thinner than the wavelength(s) of light being used to irradiate them, whereby producing clear emulsions without requiring refractive index matching for the various fluid/liquid phases used to produce the droplets.

The invention(s) can also use centrifugation forces and/or other forces to disperse a fluid, as droplets, through multiple layers of fluids (i.e., 'continuous fluids') that are immiscible with each other, forming at least a double emulsion. The dispersed fluid is immiscible with the first continuous fluid that it encounters but can be miscible with one or more subsequent fluids it encounters. In embodiments, the dispersed fluid has a density configured to allow droplets to sink to a desired position within a collecting container. In embodiments, the refractive indices of the various phases do not have to match, and the resultant emulsion is clear. This feature of the invention is attributed to the thickness of the continuous fluid surrounding each droplet being less than the characteristic wavelength(s) of light used to interrogate the sample.

The invention(s) also provide methods and systems for generating clear emulsions using multiple continuous fluid phases, each having different density characteristics, where the clear emulsions are generated upon interacting formed droplets with the multiple continuous fluid phases.

The invention(s) also provide methods and systems for forming clear emulsions with discrete droplets that are stable across ranges of temperatures for various applications (e.g., nucleic acid processing and analysis applications).

The invention(s) also provide methods and systems for positioning dispersed fluid droplets away from regions of fluid (e.g., regions containing surfactant micelles) that would otherwise prevent assessments by imaging-based interrogation modalities.

The invention(s) can also produce higher packing efficiencies than close-packing due to the thin layer of continuous phase about the dispersed phase. As such, higher packing efficiencies can enable applications where a higher percentage of the dispersed phase relative to the continuous phase is desired.

In particular, in embodiments, due to the high packing efficiency of droplets and the clarity of the emulsion in a container, the invention(s) can produce and enable fast (e.g. <a few minutes) optical analysis of a high number of droplets (e.g., from 1 million to 100 million droplets) per unit volume (e.g., 10 microliter through 100 microliters), each droplet having a characteristic diameter (e.g., 10 micron through 100 microns). In one example, the invention(s) can produce and enable fast (e.g. <a few minutes) analysis of a high number of droplets (e.g., 3.5 million droplets having a characteristic droplet diameter of 30 micron within a 50 microliter volume). In another example, the invention(s) can produce a high number of droplets (e.g., ~28 million droplets having a characteristic droplet diameter of 15 micron within a 50 microliter volume). However, variations can produce other numbers of droplets having other suitable characteristic diameters within other suitable collection volume sizes.

Applications of the invention(s) can include digital counting of nucleic acid molecules, peptide/protein molecules, cells, viral particles, living organisms, and/or other targets over a large dynamic range with low error, due to the large number of droplets available for partitioning and rapid analysis of a large number of droplets due to the clear emulsion being highly packed. In particular, the invention(s) allow droplet-based digital counting (e.g., digital PCR for analysis of nucleic acid molecules) without requiring counting of negative compartments (e.g., compartments not emitting a positive signal associated with target material), and thereby without implementing correction factors (e.g., correction factors based on Poisson statistics) for partitioning error, given that digital analysis herein can be performed in a low occupancy (e.g., ~5% or less) regime due to the availability of large number of partitions. For instance, with ~28 million droplets in a 50 microliter reaction (mean diameter ~15 micron), at ~5% of occupancy, as many as ~1.4 million nucleic acid molecules can be analyzed in a digital PCR reaction enabled by the invention(s) without having to apply Poisson statistics to correct for partitioning error.

Additionally or alternatively, the system and/or method can confer any other suitable benefit.

2. System

As shown in FIG. 1A, an embodiment of a system 100 for generation of an emulsion includes: a substrate 110 including a set of openings 115; a reservoir 120 facing the substrate at a first side and containing a sample fluid 130 configured for droplet formation upon interacting with the set of openings 115 of the substrate 110; and a collecting container 140 facing the substrate 110 at a second side and containing a set of fluid layers 150, wherein the set of fluid layers 150 is configured with a density gradient, wherein each fluid layer of the set of fluid layers 150 is immiscible with adjacent fluid layers of the set of fluid layers, wherein at least one of the set of fluid layers is configured to provide a thin film about individual droplets derived from the sample fluid, thereby producing clarity of the emulsion without refractive index matching of components of the emulsion, and wherein one or more of the set of fluid layers 150 is configured to provide a continuous phase surrounding a disperse phase of droplets derived from the sample fluid 130.

Figure 1B:
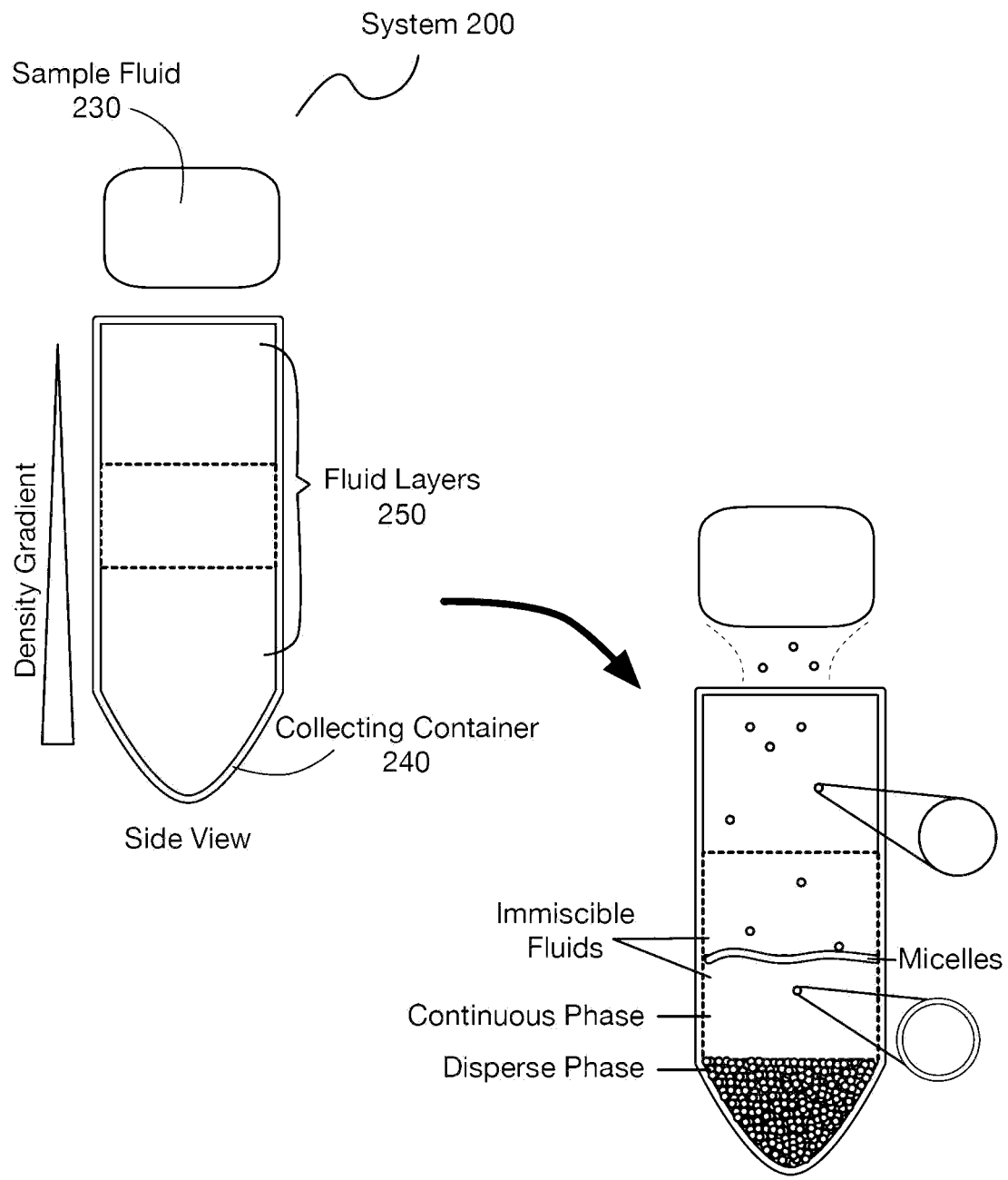
FIG. 1B depicts an alternative embodiment of a system for generating an emulsion.

Alternatively, as shown in FIG. 1B, a related embodiment of a system 200 for generation of an emulsion can include: a sample fluid 230 configured for droplet formation; and a collecting container 240 containing a set of fluid layers 250, wherein the set of fluid layers 250 is configured with a density gradient, wherein each fluid layer of the set of fluid layers 250 is immiscible with adjacent fluid layers of the set of fluid layers 250, wherein at least one of the set of fluid layers is configured to provide a thin film about individual droplets derived from the sample fluid, thereby producing clarity of the emulsion without refractive index matching of components of the emulsion, and wherein one or more of the set of fluid layers 250 is configured to provide a continuous phase surrounding a disperse phase of droplets derived from the sample fluid 230.

Embodiments of the system 100 function to form emulsions having suitable clarity for interrogation (e.g., by an imaging apparatus) without requiring refractive index (RI) matching between fluid components of the emulsions. Embodiments of the system 100 also function to facilitate processes that are less subject to manual error (e.g., pipetting error). Embodiments of the system 100 also function to form emulsions having suitable clarity and with discrete droplets that are stable across ranges of temperatures for various applications (e.g., nucleic acid processing and analysis applications). The system 100 can also function to position dispersed fluid droplets away from regions of fluid (e.g., regions containing surfactant micelles) that would otherwise obstruct interrogation (e.g., by imaging apparatus).

In various applications, the system 100 can produce emulsions having suitable clarity for enabling readout of analytes encapsulated in the dispersed phase of the emulsion, within a closed container used to collect the dispersed phase. Such a configuration mitigates sample loss and/or sample contamination that occurs using other methods of generating emulsions. In variations, readout of fluorescent signals (e.g., from labeled analytes within droplets of the dispersed phase, from products of analytes within droplets of the dispersed phase, etc.) can be performed by one or more of a 3D scanning technique (e.g., light sheet imaging, confocal microscopy, etc.) and a planar imaging technique (e.g., to take images of a cross-section of the closed container). Additionally or alternatively, in a some applications, a readout of colorimetric changes associated with droplets of the dispersed phase can be performed by 3D imaging techniques (e.g., 3D brightfield construction using light field imaging, etc.).

In other variations, readout of non-fluorescent signals from droplets of the dispersed phase can be performed. For instance, products resulting from reactions within individual droplets of the dispersed phase can produce changes in refractive indices, light absorption, light scattering, light reflection, light transmission, and/or other light interaction characteristics that are different from empty or unreacted droplets, for detection by various techniques (e.g., spectrophotometric techniques, turbidimetric techniques, etc.).

For instance, in relation to applications involving DNAs, RNAs, aptamers against proteins, chemical groups, and/or other targets, any one or more of: labeling of a target analyte or amplified version of the target analyte with fluorescent probes or dyes (e.g., hydrolysis probes, TaqMan probes, fluorescence resonant energy transfer (FRET) probes, fluorescent in situ hybridization (FISH) probes, DNA intercalating dyes etc.), labeling of probes (e.g., using digoxigenin (DIG), using biotin), labeling by way of fluorescently labeled nucleotides, labeling with DNA/RNA/ssDNA-specific dyes, or detecting by-products of DNA amplification (e.g., pH changes using pH-sensitive dyes, pyrophosphatase build up, etc.) can produce detectable/amplifiable signals (e.g., fluorescence, changes in color, with conjugation of an antibody of alkaline phosphatase or peroxidase) that are detectable from droplets of a dispersed phase produced according to the systems and methods described.

In relation to applications involving proteins, fluorescently labeled antibodies against target analytes or labeled probes (e.g., using DIG, using biotin) can produce detectable/amplifiable signals (e.g., fluorescence, changes in color, with conjugation of an antibody of alkaline phosphatase or peroxidase) that are detectable from droplets of a dispersed phase produced according to the systems and methods described.

In relation to applications involving cells, organelles, micro-organisms, viruses, or exosomes, processing with stains (e.g., live-dead stains), by cell type, by function, by detection of specific proteins (as described above), by DNAzymes, or by other processes can produce detectable/amplifiable signals that are detectable from droplets of a dispersed phase produced according to the systems and methods described.

In specific applications, the emulsion(s) generated by the systems and methods described can be used for one or more of: detection and counting of nucleic acid molecules via amplification of individual nucleic acid molecule captured within a droplet followed by detection of optically detectable signals (e.g., amplification by polymerase chain reaction (PCR) methods, by isothermal methods such as loop-mediated isothermal amplification (LAMP), by recombinase polymerase amplification (RPA), by helicase dependent amplification (HDA), by strand displacement amplification (SDA), by nicking enzyme amplification (NEAR), by transcription mediated amplification (TMA), by RNaseH mediated amplification, by whole genome amplification (WGA) using phi29, by rolling circle amplification, etc.) on purified DNA, cDNA, RNA, oligonucleotide tagged antibodies/proteins/small molecules, or directly from lysate (e.g., blood lysate); fluorescent in situ hybridization (FISH) with fluorescently tagged nucleic acids (e.g., PNA, LNA, DNA, RNA, etc.) or an indirect in situ hybridization approach using DIG or biotin, where the signal is later amplified by conjugation of an antibody to alkaline phosphatase or a peroxidase to produce a change in color detected by one or more substrates (e.g., nitroblue tetrazolium (NBT), 5-bromo-4-chloro-3-indolyl-phosphate (BCIP), HNPP, etc.); an in vitro transcription or translation assay whereby a colorimetric or fluorescent reporter is used for detection; droplet PCR applied to samples derived from single cells (e.g., prokaryotes, eukaryotes), organelles, viral particles, and exosomes; enumeration of protein or peptide molecules (e.g., by proximity ligation assays, etc.); sequencing applications (e.g., single molecule sequencing applications); monitoring or detection of products (e.g., proteins, chemicals) released from single cells (e.g., interleukin released from immune cells); monitoring cell survival and/or division for single cells; monitoring or detection of enzymatic reactions involving single cells; antibiotic resistance screening for single bacteria; enumeration of pathogens in a sample (e.g., in relation to infections, sepsis, in relation to environmental and food samples, etc.); enumeration of heterogeneous cell populations in a sample; enumeration of individual cells or viral particles (e.g., by encapsulating cells in droplets with species-specific antibodies coupled with enzymes that react with substrate components in the droplet to produce signals, etc.); monitoring of viral infections of a single host cell; liquid biopsies and companion diagnostics; prenatal diagnosis of genetic disorders (e.g., aneuploidy, genetically inherited diseases) such as with cell-free nucleic acids, fetal cells, or samples containing mixtures of fetal and maternal cells; detection of cancer forms from various biological samples (e.g., detection of cancer from cell-free nucleic acids, tissue biopsies, biological fluids, faeces); detection and/or monitoring of minimal residual diseases; monitoring responses to therapies; detection or prediction of rejection events of transplanted organs; other diagnostics associated with other health conditions; other characterizations of statuses of other organisms; and other suitable applications.

In particular, in embodiments, due to the high packing efficiency of droplets and the clarity of the emulsion in a container, the invention(s) can produce and enable fast (e.g. <a few minutes) optical analysis of a high number of droplets (e.g., from 1 million to 100 million droplets) per unit volume (e.g., 10 microliter through 100 microliters), each droplet having a characteristic diameter (e.g., 10 micron through 100 microns). In one example, the invention(s) can produce and enable fast (e.g. <a few minutes) analysis of a high number of droplets (e.g., 3.5 million droplets having a characteristic droplet diameter of 30 micron within a 50 microliter volume). In another example, the invention(s) can produce a high number of droplets (e.g., ~28 million droplets having a characteristic droplet diameter of 15 micron within a 50 microliter volume). However, variations can produce other numbers of droplets having other suitable characteristic diameters within other suitable collection volume sizes.

Applications of the invention(s) can include digital counting of nucleic acid molecules, peptide/protein molecules, cells, viral particles, living organisms, and/or other targets over a large dynamic range with low error, due to the large number of droplets available for partitioning and rapid analysis of a large number of droplets due to the clear emulsion being highly packed. In particular, the invention(s) allow droplet-based digital counting (e.g., digital PCR for analysis of nucleic acid molecules) without requiring counting of negative compartments (e.g., compartments not emitting a positive signal associated with target material), and thereby without implementing correction factors (e.g., correction factors based on Poisson statistics) for partitioning error, given that digital analysis herein can be performed in a low occupancy (e.g., ~5% or less) regime due to the availability of large number of partitions. For instance, with ~28 million droplets in a 50 microliter reaction (mean diameter ~15 micron), at ~5% of occupancy, as many as ~1.4 million nucleic acid molecules can be analyzed in a digital PCR reaction enabled by the invention(s) without having to apply Poisson statistics to correct for partitioning error.

Extensions of the systems and methods described for producing emulsions with suitable clarity can further be applied to other industries (e.g., the cosmetic industry, food industries, other chemical processing industries, etc.). Extensions of the systems and methods described can also be applied to production of microparticles, where the microparticles either have solid cores with functionalized surfaces (e.g. by surrounding droplets with a dispersed phase that can be polymerized with functional groups in the first encountered fluid of the set of fluid layers) or hollow cores with shells (e.g., by surrounding droplets of the dispersed phase with one or more layers carrying polymerizable components, thereby forming a polymer shell about a fluid core). Extensions of the systems and methods described can also be applied to synthetic biology for generation of synthetic biological components. For instance, the systems and methods can be adapted to produce synthetic cells, giant unilamellar phospholipid vesicles (GUVs), polymersomes, liposomes, exosomes, multiple layer of synthetic cells forming artificial tissue/organs, or other synthetic biology components. Extensions of the systems and methods can also be used to generate dispersions of microparticles captured within shells. Extensions of the systems and methods described can also be applied to the pharmaceutical industry. For instance, the systems and methods described can generate controlled release drug solutions (e.g., by surrounding droplets of the dispersed phase that carry drug components with one or more layers carrying reactants that can be used to trigger drug release by exposure to light, heat, changes in pH, chemical activators, mechanical forces, etc.). Additionally or alternatively, the systems and methods described can generate compositions where undesired tastes or odors of a core fluid are masked by a shell layer of fluid of the emulsion (e.g., with respect to food and pharmaceutical applications). Additionally or alternatively, the systems and methods described can involve continuous phase-carrying reactants, where the reactants can diffuse into droplets of the disperse phase when the droplets reach the continuous phase, thereby producing chemical reactions within the droplets of the disperse phase.

Extensions of the systems and methods described can produce higher packing efficiencies than close-packing due to the thin layer of continuous phase about the dispersed phase. As such, higher packing efficiencies can enable applications where a higher percentage of the dispersed phase relative to the continuous phase is desired.

Extensions of the systems and methods described can, however, be applied to other fields as appropriate.

Embodiments, variations, and examples of the system 100 are configured for execution of one or more steps of the method 300 described in Section 3 below; however, embodiments, variations, and examples of the system 100 can alternatively be configured to execute another suitable method.

2.1 System—Substrate

As shown in FIG. 1A, the system 100 can include a substrate 110 including a set of openings 115, which collectively function to produce droplets from a sample fluid when the sample fluid passes through the set of openings 115 (e.g., under applied force). As shown in FIG. 1A, the substrate 110 can be configured to interface with a reservoir 120 containing the sample fluid 130, and to allow droplets generated by the set of openings 115 to be transmitted into the collecting container 140 (described in more detail below).

The system 100 can be configured such that the sample fluid is driven through the opening(s) of the substrate 110 under an applied force. In variations, the applied force can be attributed to one or more of an applied pressure (e.g., pressurized gas driven by a pumping element, driven by a syringe, etc.), centrifugation, to applied electric fields, and other mechanisms for actively driving fluid flow. In specific examples, the applied force can be applied by centrifugation apparatus, where centrifugation can be performed using a swing bucket (i.e., in which centrifugal forces are along the longitudinal axis of the collecting container), or by using a fixed angle rotor (i.e., in which centrifugal forces are at an angle relative to the longitudinal axis of the collecting container). Additionally or alternatively, the system 100 can be configured such that the sample fluid is flows through the opening(s) of the substrate 110 passively (e.g., due to normal gravitational forces, due to capillary effects, due to electric forces, etc.).

In variations, the substrate 110 can be configured as a plate, membrane, or mesh, and the set of openings 115 can include one or more openings, each having a characteristic dimension (e.g., width, diameter), that ranges from 0.05 um to 500 um. The openings can be uniform in morphology with respect to each other, or can alternatively have non-uniform morphology (e.g., with a defined average dimension having variability within a threshold tolerance level). Each of the one or more openings can have a channel axis preferentially aligned with a longitudinal axis of the collecting container 140. Alternatively, at least one of the one or more openings can have a channel axis that is non-parallel to (e.g., at an angle to, transverse to, etc.) a longitudinal axis of the collecting container 140, for instance, in applications involving step emulsification. In variations, an opening of the one or more openings can have a cross-sectional morphology that is constant along its respective channel axis; alternatively, an opening of the one or more openings can have a cross-sectional morphology that is non-constant along its respective channel axis.

The substrate 110 can be retained in position by way of at least one of the reservoir 120 and the collecting container 140, or retained in another suitable manner or by another suitable element of the system 100.

The substrate 110 can be composed of a material having suitable mechanical properties (e.g., in terms of compliance, in terms of hardness, in terms of moduli, etc.), surface properties (e.g., hydrophobicity, hydrophilicity, porosity, charge, etc.), physical properties (e.g., in relation to reactivity with components of the sample fluid), in terms of optical properties, in terms of thermal properties (e.g., in terms of heat transfer coefficients, in terms of coefficients of expansion, etc.), and/or other properties.

In variations, the substrate 110 can be composed of one or more of: glass, quartz, a metallic material (e.g., stainless steel), a polymeric material, or a natural material. In specific examples, the substrate 110 can be composed of one or more of: glass (e.g., controlled pore glass, glass fiber, another silica-derived material), another porous glass membrane (e.g., Shirasu porous glass membrane), a metal (e.g., aluminum, silver, stainless steel, etc.), a semiconductor-derived material (e.g., silicon, silicon nitride), and a polymer (e.g., polyacrylonitrile, PVDF, cellulose acetate, polyester PETE, polyimide, PTFE, polycarbonate PCTE, polypropylene, etc.).

In embodiments, variations, and examples, the substrate 110 can include be configured as described in U.S. application Ser. No. 16/309,092 titled "Method for preparing microchannel array plate, device for obtaining liquid drops using the micro-channel array plate, and method for generating liquid drops", which is herein incorporated in its entirety by this reference. Alternatively, the substrate 110 can be configured in another suitable manner.

Additionally or alternatively, in relation to FIG. 1B and other methods droplet generation, the system 100 can omit embodiments, variations, and examples of the substrate 110 described above. For instance, the system 100 can be configured to generate droplets from a sample fluid by way of other microfluidic elements (e.g., channels), by use of needles (e.g., stainless steel needle instruments, needles composed of another suitable/non-reactive material, etc., by use of capillary instrument (e.g., pulled glass capillary pipettes, other capillary instruments, etc.), by atomization, by electrodynamic droplet formation, or by another suitable method, where the droplets are then used to form the emulsion(s) described.

2.2 System—Sample Fluid and Disperse Phase

Figure 2:
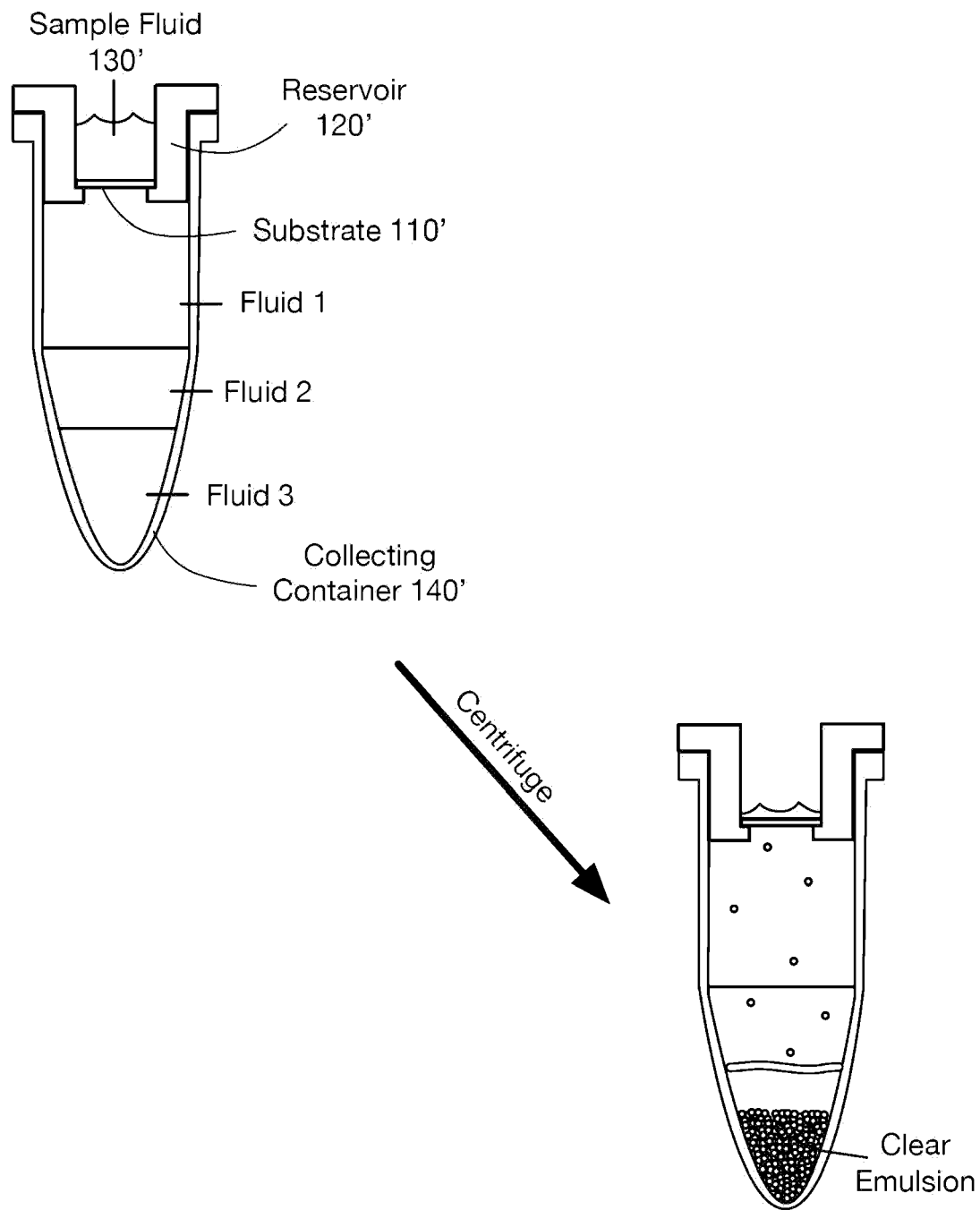
FIG. 2 depicts a specific example of a system for generating an emulsion.

As shown in FIG. 1A, the system 100 can include a reservoir 120 facing the substrate 110 at a first side and containing a sample fluid 130 configured for droplet formation upon interacting with the set of openings 115 of the substrate 110. The reservoir 120 functions to contain the sample fluid prior to generation of droplets from the sample fluid (i.e., as a dispersed phase). The reservoir 120 can also function to support the substrate 110, in order to provide an assembly that interfaces with the collecting tube 140 described below. In one variation, as shown in FIG. 1A and FIG. 2, the reservoir 120, 120' can include a base portion that supports the substrate 110, 110', and allows the sample fluid 130, 130' to pass from the reservoir 120, 120', through the set of openings of the substrate 110, 110', and into the collecting container 140, 140'. However, other variations of the reservoir 120 can be configured to interface with the substrate 110 and/or the collecting container 140 in another suitable manner.

In material composition, the reservoir 120 can be composed of one or more of: a polymer (e.g., polypropylene, polydimethylsiloxane, polystyrene, polyvinyl chloride, polymethyl methacrylate, PEEK, ABS etc.), a silicon-derived material, glass, a metallic material, a ceramic material, a natural material, a synthetic material, and/or any suitable material. The reservoir 120 can be composed of a material having suitable mechanical properties (e.g., in terms of compliance, in terms of hardness, in terms of moduli, etc.), surface properties (e.g., hydrophobicity, hydrophilicity, porosity, charge, etc.), physical properties (e.g., in relation to reactivity with components of the sample fluid), in terms of optical properties, in terms of thermal properties (e.g., in terms of heat transfer coefficients, in terms of coefficients of expansion, etc.), and/or other properties In variations where the reservoir 120 is at least partially seated within the collecting container 140, the reservoir 120 can include a protrusion defining a set position of the reservoir 120 relative to an opening of the collecting container 140 (described in more detail below), such that the reservoir 120 does not move into or out of the collecting container 140 in an undesired manner during operation. In such variations, the reservoir 120 can be configured to, with or without intermediate sealing elements, prevent fluid within the collecting container 140 from leaving the collecting container 140 at the interface between the reservoir 120 and the collecting container 140.

As described above, the reservoir 120 functions to contain the sample fluid prior to droplet generation as a dispersed phase of an emulsion. The sample fluid 130 can be an aqueous solution or can alternatively be a non-aqueous solution that is or is not miscible with water (e.g., oil, etc.), depending upon applications of use for the emulsion(s) generated. In first variations, the sample fluid 130 can be an aqueous solution. In specific examples of the first variations, the sample fluid 130 can include material associated with biological sample processing, such as: a mixture for PCR, a cell suspension, a suspension of organisms (e.g., bacteria, viruses), a nucleic acid solution (e.g., a solution of DNA for genomic amplification, a solution of RNA for reverse transcription, etc.), an amino acid or protein solution (e.g., a mixture of amino acids for synthesis, a mixture for protein crystallization, etc.), a mixture for a gelation reaction, a reagent (e.g., buffer, lysing reagent, enzyme, etc.), or another suitable aqueous solution (e.g., for another application of use).

In second variations, the sample fluid 130 is a non-aqueous liquid, and in specific examples can be a silicone oil (e.g., oligomeric dimethylsiloxane, cyclopentasiloxane, aliphatic siloxane, phenyl siloxane, fluorosiloxane, etc.), mineral oil, a hydrocarbon oil, a fluorocarbon oil, a fluorosilicone oil, another oil, a fatty acid glyceride (e.g., glyceryl dilaurate, glyceryl oleate, glyceryl linoleate, glyceryl stearate, glyceryl isostearate, glyceryl sorbate, etc.), a non-aqueous solution associated with cosmetics production, a non-aqueous solution associated with food production, a non-aqueous solution associated with a pharmaceutical application (e.g., a topical medication), or any other suitable non-aqueous liquid.

The sample fluid 130 can further be configured such that the density of the dispersed fluid is tuned in relation to the densities of one or more of the fluids in the fluid layers 150 described in more detail below. As such, the density of the dispersed fluid can be tuned such that formed droplets acquire a shell upon interaction with one or more of the fluid layers 150 and sink to an equilibrium position relative to one or more of the fluid layers 150 (e.g., after application of force by pressurization, by centrifugation, etc.). In one example, for a water-in-oil-in-water emulsion, the dispersed fluid can be tuned to have a density of >1, an oil layer can have a density <1, and an aqueous layer can have a density of ~1. In this example, the formed droplets will sink to the bottom of the collecting container 140 after applied force and acquire a thin oil shell. The densities of aqueous solutions can be tuned by adding different amounts of density medium (e.g., Optiprep™, Histodenz™, Nycodenz™, heavy water or other suitable density increasing medium).

Additionally or alternatively, in other variations, the sample fluid 130 can include a sample fluid as described in U.S. application Ser. No. 16/309,093 titled "Oil-phase composition for generating water-in-oil liquid drops by means of centrifugation", which is herein incorporated in its entirety by this reference However, in still other variations, the sample fluid 130 can include any other suitable components and/or be composed of other materials.

2.3 System—Fluid Layers as Continuous Phase(s)

As shown in FIG. 1A, the system 100 includes a collecting container 140 facing the substrate 110 at a second side and containing a set of fluid layers 150, where the collecting container 140 functions to receive droplets of the sample fluid 130, and to transmit the droplets into and/or through one or more of the set of fluid layers 150 to generate at least a double emulsion. The first fluid (other than gas) of the set of fluid layers 150 that the dispersed fluid encounters is preferably configured to be immiscible with the dispersed fluid. Furthermore, the set of fluid layers 150 functions to provide at least one stable thin film layer about each droplet of a disperse phase generated from the sample fluid 130 before the disperse phase arrives at its equilibrium position within a continuous phase of the set of fluid layers 150. As such, the arrangement and composition(s) of the set of fluid layers 150 functions to form at least double emulsions having suitable clarity for downstream analyses, due to the thickness of the thin film layers surrounding droplets being less than the wavelength(s) of light used to observe the emulsions. As such, clarity of the resulting emulsions is not attributed to refractive index (RI) matching between fluids used. The equilibrium position(s) of the droplets of the disperse phase at one or more of the set of fluid layers 150 also allows interrogation of the droplets (e.g., by using imaging apparatus, by other optical-based interrogation) for downstream applications and assessments, and allows separation of the emulsion from layers (e.g., layers containing surfactant micelles) that prevent clear observation of the emulsion at its equilibrium position.

In variations, the collecting container 140 can be a container configured for centrifugation (e.g., a centrifuge tube, a microcentrifuge tube, etc.), a process container for PCR (e.g., a PCR tube), a strip tube, a plate having wells (e.g., a microtiter plate, a multi-well plate), or another suitable collecting container for the emulsion(s) generated. Alternatively, the collecting container 140 can be a custom-designed container for generating and/or containing the emulsion prior to downstream analyses or further processing. For instance, the collecting container 140 can include one or more openings (e.g., with or without valves) for transmitting contents from the collecting container 140 and/or for receiving additional material into the collecting container 140. For instance, after an initial reaction or generation of a first emulsion, the system 100 can be configured to receive additional materials (e.g., liquids, gases, etc.) to provide additional reactions or processing steps.

Figure 3A:
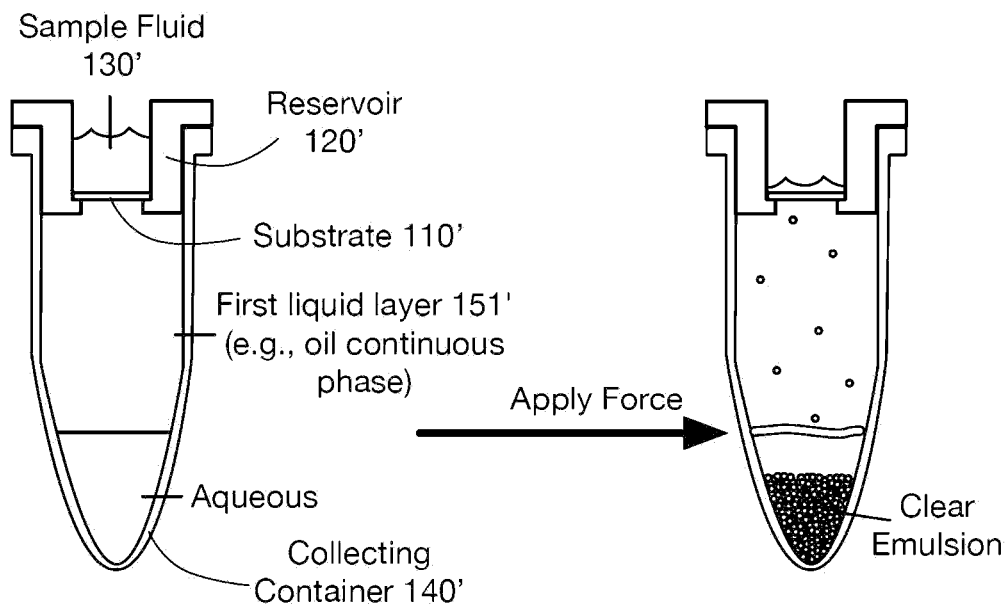
FIGS. 3A-3B depict variations of a system configuration for generating an emulsion, where
Figure 3B:
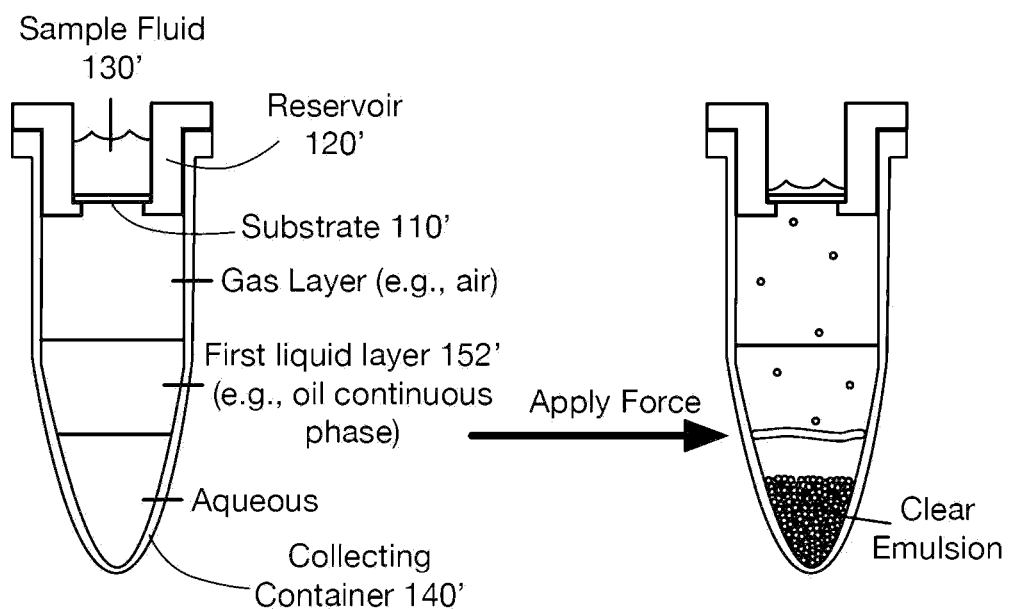

In variations, the set of fluid layers 150 is configured with a density gradient, and in the orientation shown in FIGS. 1A and 2, the densest fluid of the set of fluid layers 150 is located at the base of the collecting container 140, and the least dense fluid of the set of fluid layers 150 is located furthest from the base of the collecting container 140. As shown in FIG. 3A, the least dense layer of the set of fluid layers 150 can be a liquid phase material, such that droplets of the sample fluid 130' are transmitted directly into a first liquid layer 151' of the set of fluid layers without passing through another layer. In this variation, the substrate 110' and/or reservoir 120' described above can be at least partially submerged in the first liquid layer 151 of the set of fluid layers 150. Alternatively, as shown in FIG. 3B, the least dense layer of the set of fluid layers 150 can be a gas phase material (e.g., air, another gas), such that droplets of the sample fluid 130' are transmitted into a first liquid layer 152 of the set of fluid layers 150 by first passing through a gas layer. In this variation, the substrate 110 and/or reservoir 120 described above may not be at least partially submerged in the first liquid layer 152 of the set of fluid layers 150 and may instead be separated from the first liquid layer 152 by a gap (e.g., of air).

Furthermore, each fluid layer of the set of fluid layers 150 is preferably immiscible with adjacent fluid layers of the set of fluid layers 150, such that the layers of the set of fluid layers 150 are substantially discrete in relation to each other. Alternatively at least one of the set of fluid layers 150 can be miscible with an adjacent fluid layer (e.g., but with a different density compared to the adjacent fluid layer), such that there is a non-discrete boundary between the adjacent fluid layers. Alternatively, the set of fluid layers can include adjacent fluid layers that are both aqueous solutions, but non-miscible with each other (e.g., as aqueous multi-phase systems).

In relation to composition, alternating fluid layers of the set of fluid layers 150 can include aqueous solutions and/or non-aqueous solutions. In variations, aqueous solutions of the set of fluid layers 150 can include material associated with biological sample processing, such as: material for PCR, a suspension of particles (e.g., particles with binding moieties) or other biological material, a nucleic acid solution (e.g., a solution of DNA for genomic amplification, a solution of RNA for reverse transcription, etc.), an amino acid or protein solution (e.g., a mixture of amino acids for synthesis, a mixture for protein crystallization, etc.), a mixture for a gelation reaction, a reagent (e.g., buffer, lysing reagent, enzyme, etc.), or another suitable aqueous solution (e.g., for another application of use). In one example, an aqueous continuous phase can be composed of water/heavy water or a suitable buffer (e.g., saline buffer), where the dispersed phase (e.g., droplets) are composed of a PCR mix with a density medium. Furthermore, in this example, a solute (e.g., simple sugar molecules) were added to the aqueous phase in order to balance osmolarity of the aqueous solution with the PCR mix, in order to prevent osmosis or droplet expansion over time.

In variations, non-aqueous liquids of the set of fluid layers 150 can include one or more of (e.g., including blends of): a silicone oil (e.g., oligomeric dimethylsiloxane, cyclopentasiloxane, aliphatic siloxane, phenyl siloxane, fluorosiloxane, etc.), mineral oil, a hydrocarbon oil, a fluorocarbon oil, a fluorosilicone oil, another oil, a fatty acid glyceride (e.g., glyceryl dilaurate, glyceryl oleate, glyceryl linoleate, glyceryl stearate, glyceryl isostearate, glyceryl sorbate, etc.), a non-aqueous solution associated with cosmetics production, a non-aqueous solution associated with food production, a non-aqueous solution associated with a pharmaceutical application (e.g., a topical medication), or any other suitable non-aqueous liquid. Additionally or alternatively, in variations, one or more of the set of layers 150 can include a gas-phase material, a solid-phase material, or any other suitable phase of material.

In relation to generation of emulsions, one or more of the set of fluid layers 150 (e.g., continuous phase(s) of the set of fluid layers 150) can include a surfactant, fluorosurfactant (e.g., containing a perfluoroalkyl group, etc.), and/or emulsifier to promote generation of stable emulsions. In examples, the surfactant(s) and/or emulsifiers used can include one or more of: a Tween® (e.g., Tween® 20, Tween® 21, Tween® 40, Tween® 60, Tween® 61, Tween® 65, Tween® 80, etc.), a Span® (e.g., Span® 20, Span® 40, Span® 60, Span® 80, Span® 83, Span® 85, Span® 120, etc.), an Abil® (e.g., Abil® we09, Abil® em90, Abil® em120, Abil® em180, etc.), Dow Corning® 5200, Dow Corning ES-5612, Dow Corning® ES-5300, Dow Corning ES-5600, Dow Corning® emulsifier 10, DehymuLs® SML, Cremophor® WO 7, Isolan® GI 34, Isolan® GIPDI, Tegosofit® Alkanol S 2, Triton™ (e.g. Triton X-100), IGEPAL™ CA-630/NP-40, and another suitable surfactant/ fluorosurfactant/emulsifier. In one example, a non-aqueous continuous phase (e.g., non-aqueous continuous phase where there is a distribution of continuous phases used) can be composed of a silicone oil blend with surfactants.

Figure 4A:
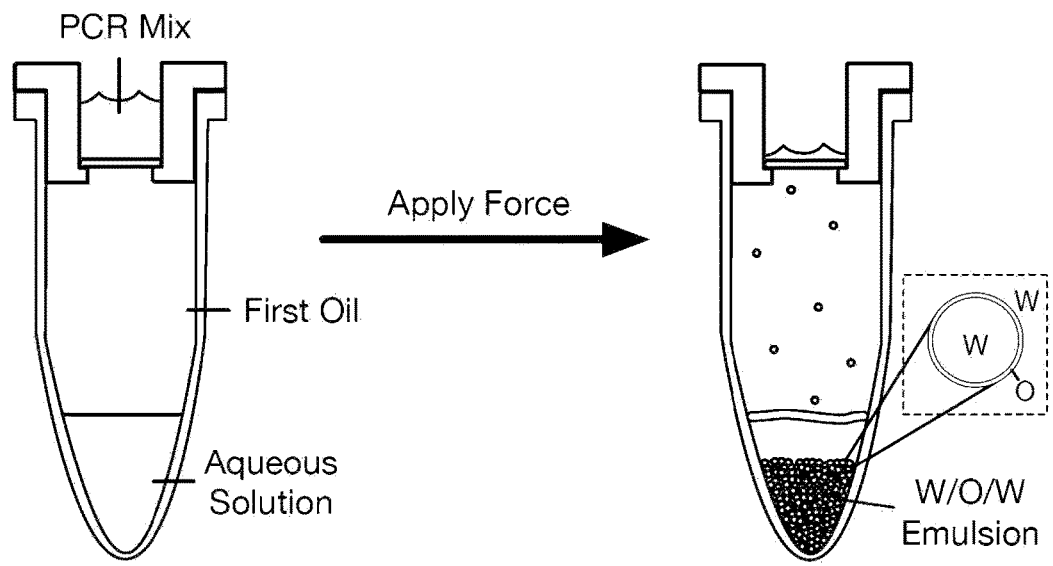
FIGS. 4A-4B depict variations of emulsions, where
Figure 4B:
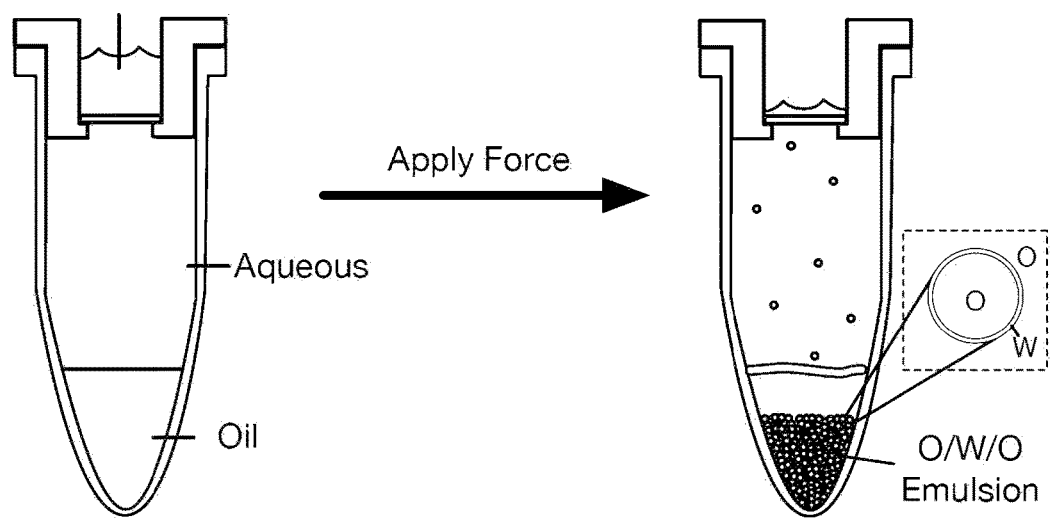

Additionally or alternatively, in other variations, one or more of the set of fluid layers can include a composition as described in U.S. application Ser. No. 16/309,093 titled "Oil-phase composition for generating water-in-oil liquid drops by means of centrifugation", which is herein incorporated in its entirety by this reference In variations, the set of fluid layers 150 can include two fluid layers, three fluid layers, four fluid layers, or greater than four fluid layers, where each layer has suitable thickness and/or volume to provide suitable amounts of transit time for droplets and/or amounts of material for generating stable emulsions. Additionally or alternatively, multiple fluid layers can be used to position generated droplets (e.g., generated droplets and a bottom or top surface of the collecting container 140, 140', where methods described further below cover variations of methods for generating clear emulsions using multiple immiscible continuous phases having different densities in relation to density of the dispersed phase. In a first variation, as shown in FIG. 4A, the sample fluid is an aqueous solution (e.g., PCR mixture/ solution) and the set of fluid layers includes a first oil (to generate a thin film about droplets of the sample fluid) and a second aqueous solution (e.g., equilibrium continuous phase), which functions to receive droplets that have passed through the first oil in order to form a water-in-oil-in-water (W/O/W) emulsion with suitable clarity. In another variation, as shown in FIG. 4B, the sample fluid 130 is a non-aqueous solution that is immiscible with water, and the set of fluid layers 150 includes a first aqueous solution (to generate a thin film about droplets of the sample fluid) and a second non-aqueous solution (e.g., equilibrium continuous phase of oil), which functions to receive droplets that have passed through the first aqueous solution in order to form an oil-in-water-in-oil (O/W/O) emulsion with suitable clarity. However, in other still other variations, the set of fluid layers 150 can include other suitable numbers and compositions of fluids for forming W/O/W/ . . . /W emulsions, W/O/W/ . . . /O emulsions, O/W/O/ . . . /O emulsions, or O/W/O/ . . . /W emulsions having any other suitable numbers of layers of the disperse phase and an appropriate composition of the continuous phase. Stable density gradients in the fluids used, as well as having an oil film at the outermost layer of each droplet of the dispersed phase can contribute to emulsion stability as well.

Figure 5A:
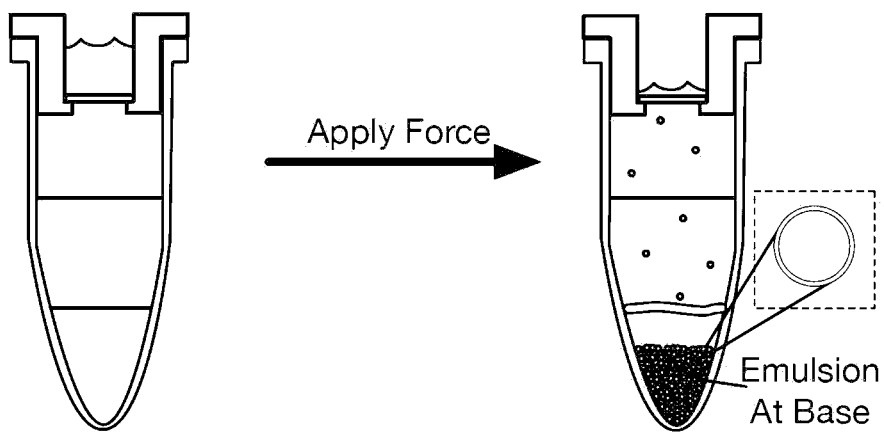
FIGS. 5A-5C depict variations of equilibrium emulsion positions within a collecting container.
Figure 5B:
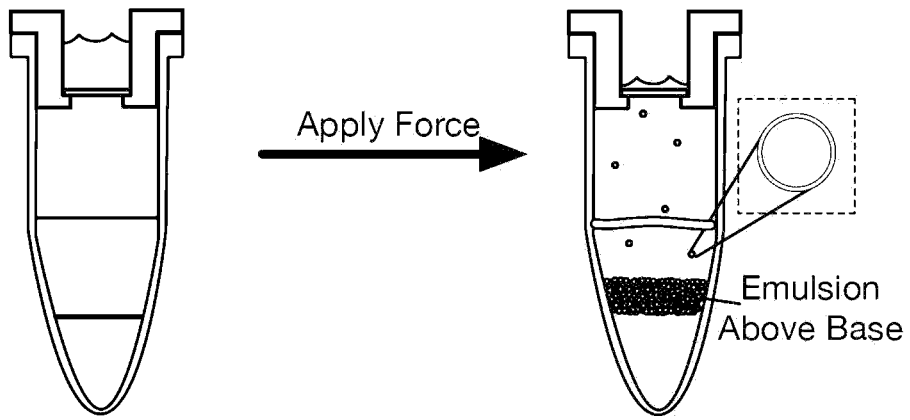
Figure 5C:
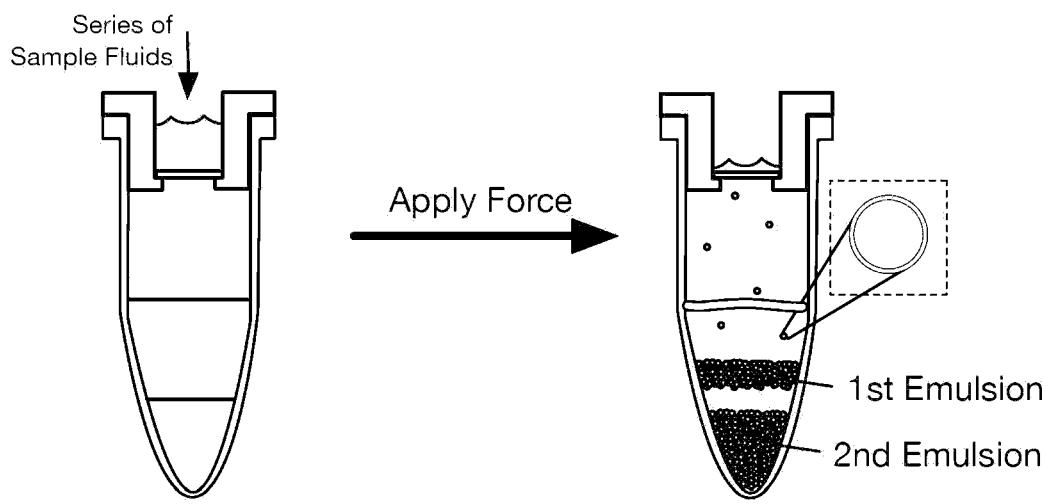

As shown in FIG. 5A, the resulting density of the disperse phase after interacting with one or more fluid layers of the set of fluid layers can be greater than densest layer of the set of fluid layers, such that the emulsion ultimately rests at the base of the collecting container. Alternatively, the resulting density of the disperse phase after interacting with one or more fluid layers of the set of fluid layers can be less than that of the densest layer of the set of fluid layers, such that the emulsion does not ultimately rest at the base of the collecting container. Still alternatively, as shown in FIG. 5C, in variations where emulsions of different compositions are collected within a single collecting container, the arrangement and compositions of the set of fluid layers can be configured such that the system 100 generates a first emulsion that has an equilibrium position in one layer of the set of fluid layers, and a second emulsion that has an equilibrium position in a second layer of the set of fluid layers.

The system 100 can, however, additionally or alternatively include other elements and/or configurations of elements for generation of stable emulsions without requiring RI matching to have suitable clarity for downstream analyses.

3. Method

As shown in FIGS. 6A and 6C, an embodiment of a method 300 for generation of an emulsion includes: generating a set of droplets from a sample fluid 310; and generating the emulsion upon processing the set of droplets with a set of fluid layers 320 (e.g., to provide a thin film about each droplet, thereby forming at least a double emulsion), wherein the set of fluid layers is configured with a density gradient. In variations wherein processing the set of droplets includes dispersing the set of droplets through the set of fluid layers, each fluid layer of the set of fluid layers is immiscible with adjacent fluid layers of the set of fluid layers, and at least one of the set of fluid layers can be configured to provide a thin film about individual droplets derived from the sample fluid, thereby producing clarity of the emulsion without refractive index matching of components of the emulsion. In variations, the method 300 can additionally or alternatively include other suitable steps associated with downstream applications. The method 300 functions to provide benefits described in relation to Sections 1 and 2 above. The method 300 can be implemented using embodiments, variations, and examples of the components of the system 100 described above or can alternatively be implemented using other suitable system components.

As shown in FIG. 6A, the method 300 includes generating a set of droplets of a sample fluid 310, where embodiments, variations, and examples of system components for generating droplets from a sample fluid are described above. The set of droplets can be generated from an aqueous solution or a non-aqueous solution, where compositions of aqueous and non-aqueous sample fluids are described above. Additionally or alternatively, in variations, generating the set of droplets 310 can include implementing one or more of: microfluidic elements (e.g., channels), needle instruments (e.g., stainless steel needle instruments, needles composed of another suitable/non-reactive material, etc., capillary instruments (e.g., pulled glass capillary pipettes, capillary plates, other capillary instruments, etc.), meshes, filter membranes, nebulizers, atomizers, electrodynamic droplet formation devices, and/or other suitable methods, where the droplets are then used to form the emulsion(s) described.

Alternatively, as shown in FIG. 6C, generating the set of droplets 310' can be performed according to another suitable method. Similarly, in variations, generating the set of droplets 310' can include implementing one or more of: microfluidic elements (e.g., channels), needle instruments (e.g., stainless steel needle instruments, needles composed of another suitable/non-reactive material, etc., capillary instruments (e.g., pulled glass capillary pipettes, capillary plates, other capillary instruments, etc.), filter membranes, meshes, nebulizers, atomizers, electrodynamic droplet formation devices, and/or other suitable methods, where the droplets are then used to form the emulsion(s) described. In variations, the generated droplets (e.g., as a dispersed phase), can have a density greater than that of the continuous phase (i.e., first continuous phase described in more detail below) into which they enter. However, in other variations, the generated droplets can have another suitable density.

3.1 Emulsion Generation—First Variation

As shown in FIG. 6A, the method 300 also includes generating an emulsion upon processing the set of droplets with a set of fluid layers 320. In one variation, generating the emulsion can include dispersing the set of droplets through a set of fluid layers 320, where the set of fluid layers is configured with a density gradient and wherein each fluid layer of the set of fluid layers is immiscible with adjacent fluid layers of the set of fluid layers. Step 320 functions to generate emulsions having suitable clarity without requiring RI matching between fluid components of the emulsion. In particular, Step 320 functions to generate at least one stable thin film layer about each of the set of droplets generated from the sample fluid, where clarity of the resultant emulsions is due to the thickness of the thin film layers surrounding droplets being less than the wavelength(s) of light used to observe the emulsions. In relation to step 320, the equilibrium position(s) of the set of droplets of the disperse phase at one or more of the set of fluid layers also allows interrogation of the droplets (e.g., by using imaging apparatus) for downstream applications and assessments, and allows separation of the emulsion from layers (e.g., layers containing surfactant micelles) that prevent clear observation of the emulsion at its equilibrium position.

In more detail, dispersing in step 320 can include applying a force (e.g., centrifugation, pressure, etc.) to the sample fluid in order to disperse the sample fluid through a substrate including a distribution of holes, followed by dispersion of generated droplets through one or more of the set of fluid layers (i.e., layers of continuous fluids having a distribution of densities). The dispersed sample fluid is immiscible with the first continuous fluid that it encounters but can be miscible with the second continuous fluid it encounters. In variations, the dispersed fluid can have a density higher than the bottom-most fluid layer, such that the generated droplets sink to the bottom of the collecting container. The refractive indices of the various phases do not have to match, and the resultant emulsion is clear or otherwise has suitable clarity for various applications described. Clarity characteristics are achieved due to the continuous fluid(s) surrounding each droplet is being thinner than the wavelength of light being used to illuminate the emulsion.

Embodiments, variations, and examples of configurations and compositions of the set of fluid layers, as well as resultant emulsions, are described in Section 2.3 above.

Figure 6B:
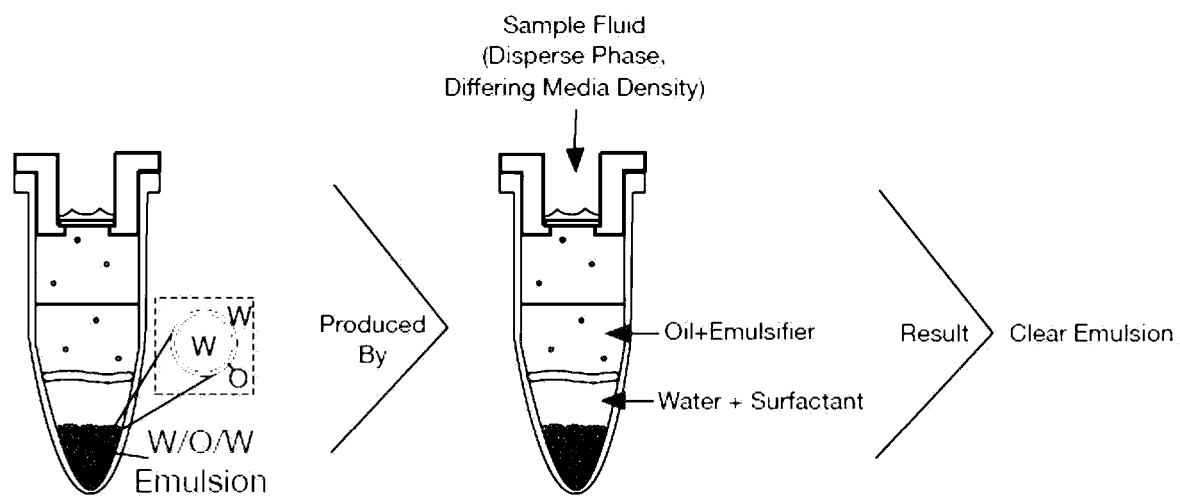
FIG. 6B depicts schematics of a variation of the first embodiment of a method for generating an emulsion.
Figure 6B:
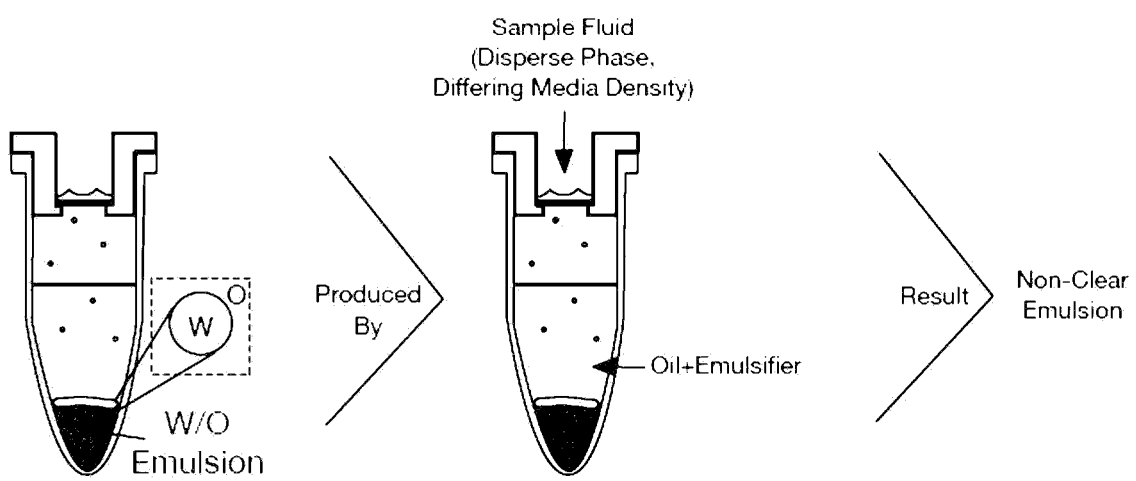

In a specific example of Step 320, as shown in FIG. 6B (top), W/O/W emulsions were generated from sample fluids composed of water with a non-ionic surfactant and between 0% and 70% Optiprep™ (a density gradient medium, however other density adjusting media can be used), where the sample fluids had various RIs between 1.33 and 1.40 (densities ~1 to >1 g/ml). The sample fluids were used to generate droplets using an example of the system 100 described above, and the droplets were transmitted through a set of fluid layers including an oil layer composed of a silicone blend mixed with a silicone-based emulsifier (having a RI of 1.39, density <1 g/ml), prior to arrival at a continuous aqueous fluid layer of water mixed with an surfactant (having a RI of 1.33, density~1 g/ml). As shown in FIG. 7 (top), the emulsions had suitable clarity regardless of the final RI of any solution used to generate the emulsions, but a distinct droplet layer did not form when the density of the sample fluid was equal to the density of the aqueous fluid layer used for the continuous phase. In comparison, FIG. 7 (bottom) depicts an example where water-in-oil emulsions were generated, and where RI matching was required to have suitable clarity of emulsions (e.g., 59% Optiprep™ in water to match the RI of the oil-based continuous phase).

3.2 Emulsion Generation—Second Variation

As shown in FIG. 6C, generating an emulsion upon processing the set of droplets with a set of fluid layers 320' can include processing droplets generated according to step 310' with at least a second continuous phase, in order to generate a clear emulsion. In variations, the result of step 310' can be an emulsion of water-in-oil droplets (e.g., with an aqueous phase dispersed in a non-aqueous continuous phase as a first continuous phase) or oil-in-water droplets (e.g., with a non-aqueous phase dispersed in an aqueous continuous phase as a first continuous phase), such that step 310' produces an early stage emulsion having clarity below a threshold level of clarity. In these variations, the dispersed phase has a density higher than that of the first continuous phase, and the result of step 310' is an emulsion having low clarity due to light scattering from the refractive index mismatches between the fluids (e.g., a cloudy emulsion).

In embodiments, clarity can be defined in units associated with clarity or turbidity (e.g., NTU, FNU), such that the threshold level of clarity can be measured for the emulsion(s) generated according to the methods described. In one variation, clarity can be characterized in relation to transmissivity as detectable by a transmission detector and/or in relation to a suitable distance or depth (e.g., depth or distance into a collecting container for the emulsion; through a depth of a container of the emulsion, along an axis in which measurement of clarity is performed, etc.), where, in variations, the threshold level of clarity of the emulsion is associated with a transmissivity greater than 70% transmissivity, greater than 80% transmissivity, greater than 90% transmissivity, greater than 95% transmissivity, greater than 99% transmissivity, etc. As such, in accordance with methods described, upon measuring clarity of the emulsion (e.g., later stage emulsion) using a transmission detector the emulsion is characterized by a clarity associated with greater than 70% transmissivity, greater than 80% transmissivity, greater than 90% transmissivity, greater than 95% transmissivity, greater than 99% transmissivity, etc., which is above the threshold level of clarity.

Additionally or alternatively, in another variation, clarity can be characterized in relation to clarity/turbidity as detectable by a turbidity measurement system (e.g., nephelometer, turbidimeter, etc.) and/or in relation to a suitable distance or depth (e.g., depth or distance into a collecting container for the emulsion; through a depth of a container of the emulsion, along an axis in which measurement of clarity is performed, etc.), where, in variations, the emulsion has a turbidity less than 10 turbidity units (e.g., nephelometric turbidity units NTU)), less than 5 turbidity units, less than 1 turbidity unit, etc. As such, in accordance with methods described, upon measuring clarity of the emulsion using a turbidity measurement system the emulsion (e.g., later stage emulsion) is characterized by a clarity associated with less than 10 NTU, less than 5 NTU, less than 1 NTU, etc., which is above the threshold level of clarity. Additionally or alternatively, turbidity can be characterized in terms of Formazin turbidity units (FTU), Helms units, parts per million, concentration units, optical density, and/or any other suitable units associated with any other suitable detection system.

After initial droplet formation according to step 310', step 320' can include processing the early stage emulsion with a second continuous phase that is immiscible with the first continuous phase and denser than the first continuous phase, in order to produce a later stage emulsion having clarity above a threshold level of clarity. Processing with the second continuous phase can include combining the second continuous phase with the early stage emulsion in a collecting container 322', and applying a force to the collecting container with the early stage emulsion and the second continuous phase to generate the later stage emulsion 323'.

In variations, the applied force can be a force applied by centrifugation (e.g., at or above 10,000 G, below 10,000 G, at another suitable angular velocity, etc.), for a duration of time (e.g., less than or equal to one minute, greater than one minute, etc.). In a specific example, applying the force in step 323' can include centrifuging the collecting container with the early stage emulsion and the second continuous phase at 16,000 G for one minute; however, variations of the specific example can be implemented. Additionally or alternatively, the applied force can be a force applied by pressurization, vibration, rocking, or any other suitable method to promote movement of the second continuous phase for interaction with contents (e.g., the dispersed phase, the first continuous phase) of the collecting container and toward an equilibrium density gradient.

In variations, the second continuous phase is denser than the first continuous phase, such that the applied force moves the second continuous phase deeper into the collecting container and displaces an excess volume of the first continuous phase in order to reduce physical distance between droplets in the dispersed droplet phase of the early stage emulsion, thereby generating a later stage emulsion having clarity above the threshold level of clarity.

Figure 6D:
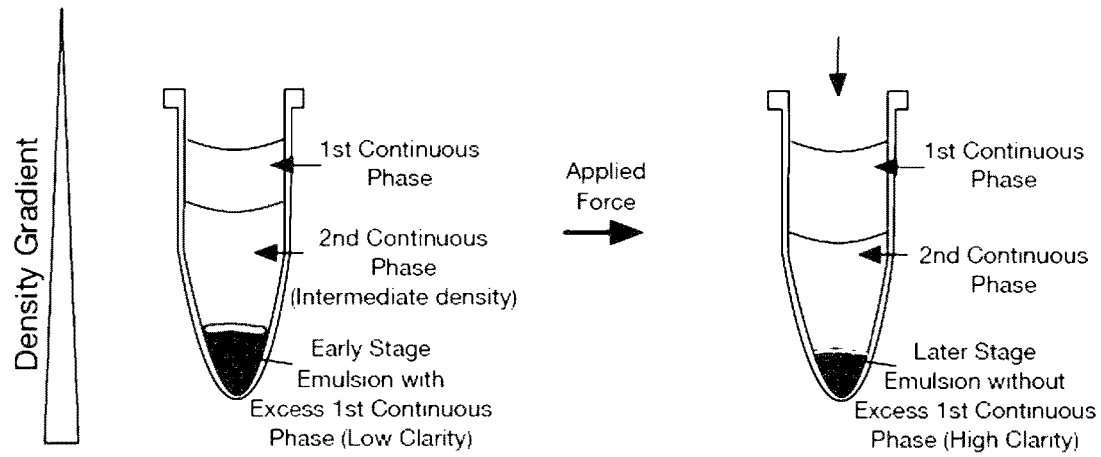
FIGS. 6D-6E depicts schematics of variations of the second embodiment of a method for generating an emulsion.

In one example shown in FIG. 6D, the second continuous phase can be denser than the first continuous phase but less dense than the dispersed droplet phase of the early stage emulsion, such that the excess volume of the first continuous phase is displaced away from the dispersed droplet phase at the base of the collecting container in generating the later stage emulsion having clarity above the threshold level of clarity. In this example, the first continuous phase is a silicone oil blend with surfactants, the second continuous phase is intermediate in density and composed of water (or a saline buffer) with a surfactant, and the dispersed droplet phase is a PCR mix with a density medium.

Figure 6E:
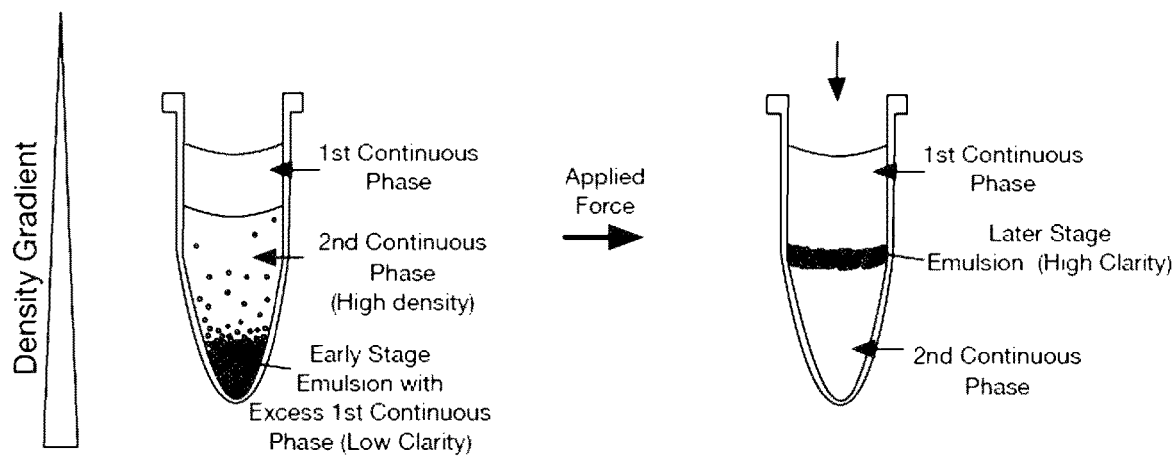

Alternatively, in another example shown in FIG. 6E, the second continuous phase can be denser than the first continuous phase and denser than the dispersed droplet phase of the early stage emulsion, such that the dispersed droplet phase settles away from the base of the collecting container (e.g., between the first continuous phase and the second continuous phase, near an air interface, etc.) in generating the later stage emulsion having clarity above the threshold level of clarity.

Variations of the method 300' can include processing intermediate stage emulsions with additional continuous phases (e.g., a third continuous phase, a fourth continuous phase, etc.) that are immiscible with each other and/or other continuous phases being used, and having suitable density characteristics, in order to produce resultant emulsions having even greater clarity or other desired properties for various applications of use.

3.3 Emulsion Generation—Droplet Digital PCR

Figure 7A:
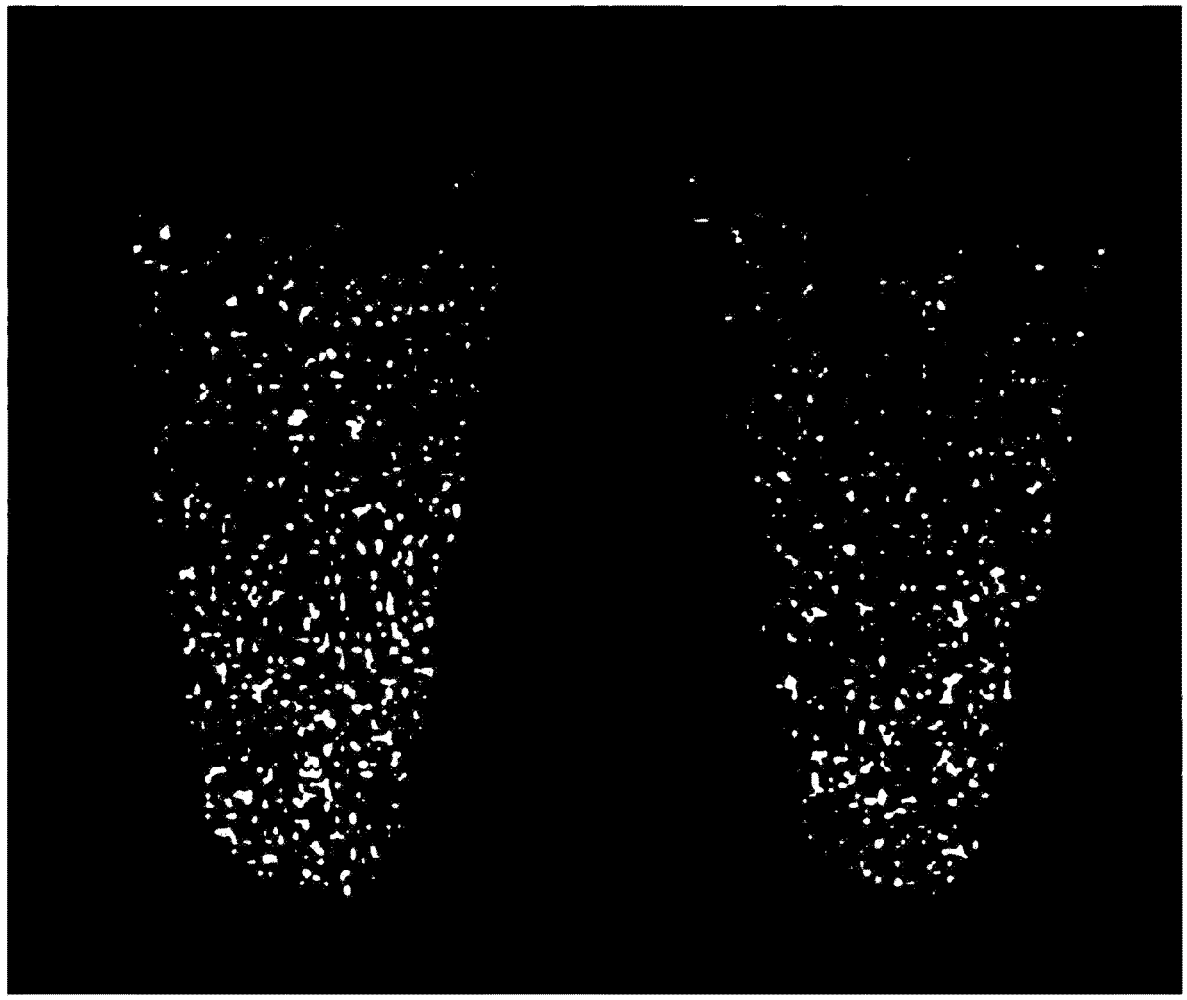
FIG. 7A depicts cross-sectional images of a collecting container (e.g., cross-sectional images toward the center of the collecting container) containing an emulsion generated according to the method, where droplets of the emulsion fluoresce in a manner that is detectable due to clarity of the emulsion.

In variations, the method 300 can additionally or alternatively include other suitable steps associated with downstream applications. Such applications can include performing one or more steps associated with PCR (e.g., thermocycling, incubating, mixing, imaging, material retrieval, etc.), in order to analyze reactions or products generated within each droplet of the disperse phase of the emulsion. For instance, as shown in FIG. 7A, the method 300 can include performing droplet digital PCR with clear emulsions produced according to steps 310 and 320 above. In particular, FIG. 7A depicts two cross-sectional images towards the center of a collecting container containing droplets that fluoresce after performing droplet digital PCR, where the cross-sectional images obtained by light sheet imaging of the tube, where light sheet imaging can be performed as described in PCT Application PCT/CN2019/093241 filed 27 Jun. 2019, which is herein incorporated in its entirety by this reference. In this example, the droplets were formed by generating droplets from 50 microliter of a PCR master mix containing polymerase, dNTPs, template DNA molecules, primers, dual-labeled hydrolysis probes. The droplets were generated by transmitting the mixture described above through a 1 mm thick glass substrate having 37 microchannels, by centrifugation at 16000 g. The formed droplets, as they exited the glass substrate, went into a 0.2 ml collecting container tube containing 50 microliter of water with surfactant (as a continuous phase), above which was a layer of 50 microliter of silicone oil blend with silicone emulsifier. Approximately 3.5 million drops were formed by this example process. In FIG. 7A, each fluorescent drop, measured to be ~30 micron in diameter, represents amplification from one target molecule, and the clarity of the emulsion generated allowed capture of clear images along each the cross-sections of the tube. The number of fluorescent drops was quantified to be ~100 k.

3.3.1 Positive Droplet PCR

Figure 7B:
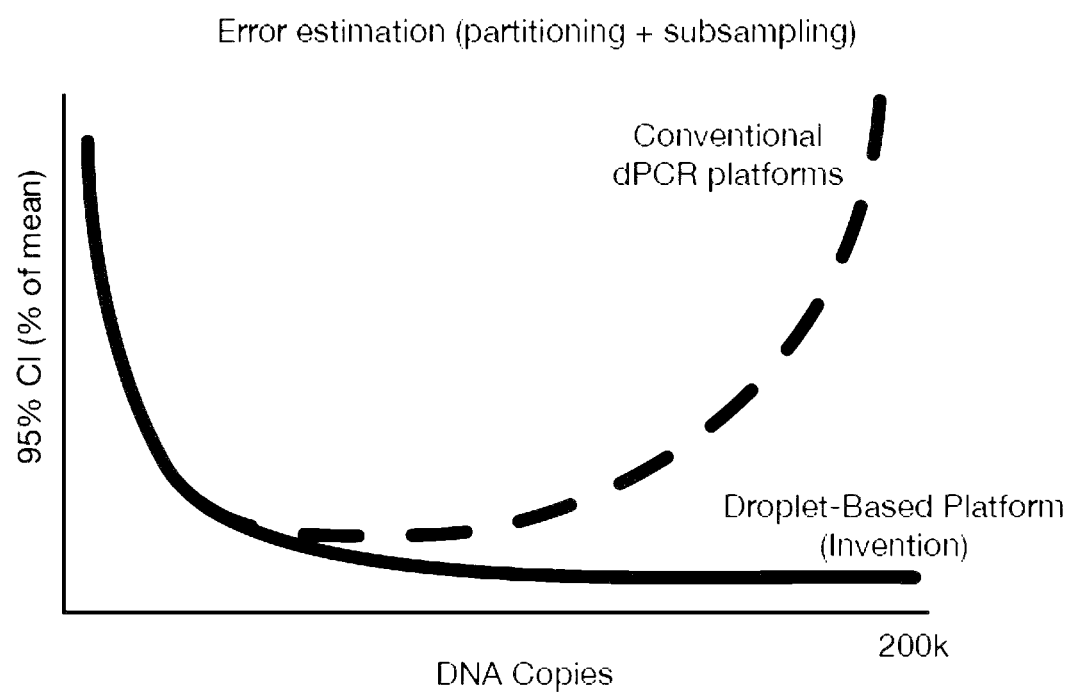
FIG. 7B depicts an example of comparative performance of embodiments of the system/method described, in relation to conventional digital PCR platforms that have high partitioning error due to limitations in the number of partitions provided.

In particular, in comparison to conventional digital PCR platforms, in which the number of partitions are limited to the 20,000 or less and require counting both positive and non-positive compartments and applying Poisson statistics to estimate counts, the invention(s) described herein do not require portioning error correction methodologies for counting applications (e.g., associated with distributions of material), due to the high number of droplets generated and operation at low occupancy (see FIG. 7B). As such, the invention(s) provide improved precision at high DNA counts with lower counting uncertainty. Such invention(s) can thus provide a droplet-based platform for high dynamic range digital PCR. Applications of method(s) described can thus include droplet-based digital PCR without requiring counting of negative droplets (e.g., droplets not containing target material), and thereby without implementing correction factors (e.g., Poisson correction factors) for partitioning error, given that performance of digital PCR herein can be performed in a low occupancy (e.g., ~5% or less total droplets are occupied by target material) regime. In particular, in embodiments, the method(s) can produce a high number of droplets (e.g., from 1 million to 100 million droplets) per unit volume (e.g., 10 microliter to 100 microliter), each droplet having a characteristic diameter (e.g., 10 micron-100 micron). In one example, the method(s) can produce a high number of droplets (e.g., 3.5 million droplets having a characteristic droplet diameter of 30 micron within a 50 microliter volume). In another example, the invention(s) can produce a high number of droplets (e.g., 28 million droplets having a characteristic droplet diameter of 15 um within a 50 ul volume). However, variations can produce other numbers of droplets (e.g., greater than 500,000 droplets/partitions) having other suitable characteristic diameters within other suitable collection volume sizes.

In particular, with respect to droplet digital PCR, methods can include steps for detecting and quantifying only droplets emitting a positive signal (e.g., with respect to target material sequences), without detecting and/or quantifying droplets having a negative signal. As such, methods described can be used for positive digital PCR, without requiring detection or quantification of droplets having a non-positive signal.

Figure 7C:
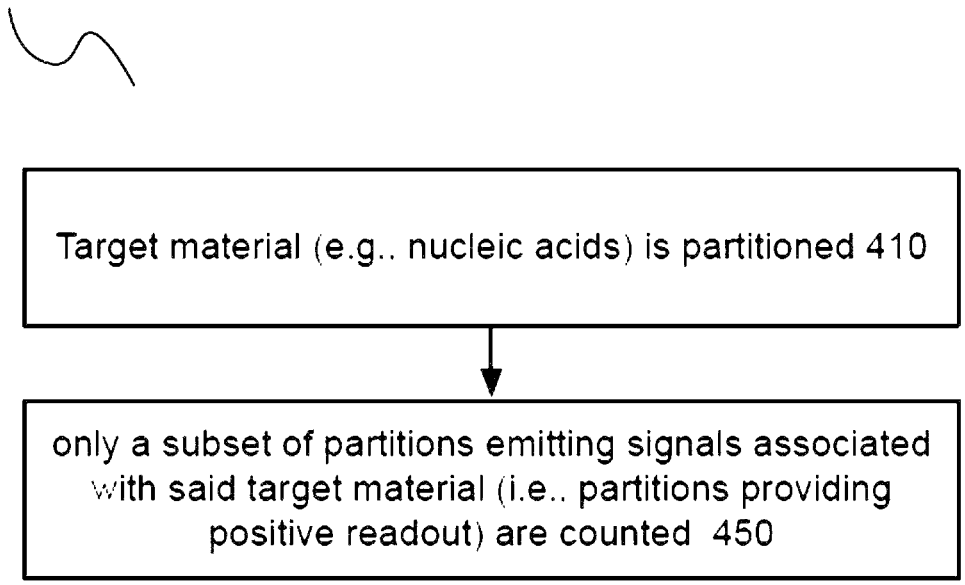
FIG. 7C depicts a flow chart of an embodiment of a method for performing droplet digital PCR.

As shown in FIG. 7C, such methods can thus include: a method 400 of counting nucleic acids in a sample (e.g., a sample of more than 5,000 nucleic acids, a sample of more than 10,000 nucleic acids, a sample of more than 20,000 nucleic acids, etc.) wherein said nucleic acids distributed across a set of partitions 410 (e.g., within droplets of an emulsion, partitioned in another manner), and wherein only a subset of the set of partitions emitting signals associated with said nucleic acids (i.e., droplets providing positive readout) are counted (and droplets not providing positive readout are not counted) 450.

Figure 7E:
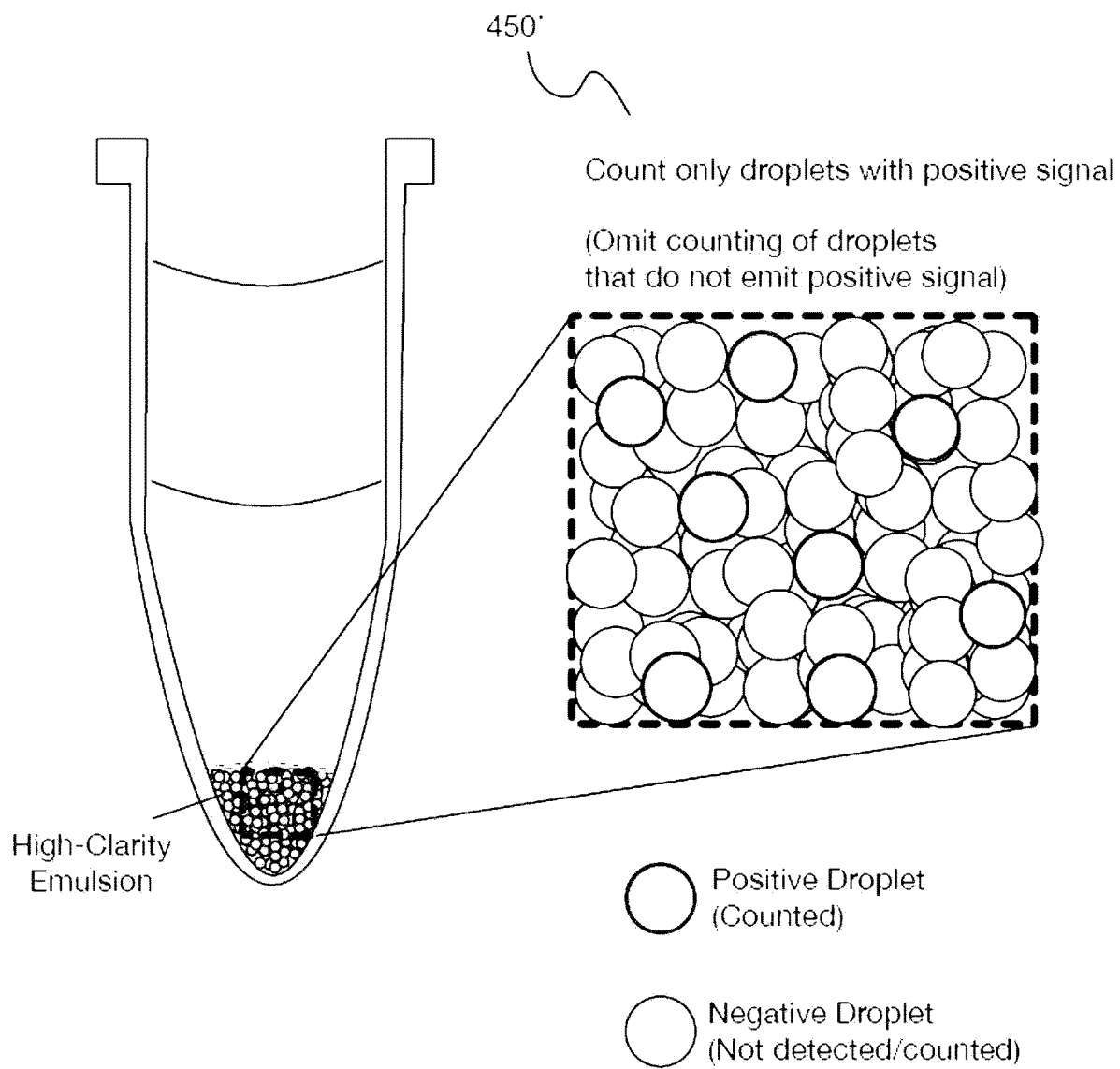
FIG. 7E depicts a schematic of an embodiment of a quantification operation in accordance with the method shown in FIG. 7D.

Relatedly, as shown in FIGS. 7D and 7E, a method 400' for performing droplet digital PCR can thus include: generating a set of droplets from a sample fluid 410'; generating an emulsion having clarity above a threshold level of clarity upon processing the set of droplets with one or more fluid layers configured with a density gradient, wherein each fluid layer of the one or more fluid layers is immiscible with adjacent fluid layers of the one or more fluid layers, thereby producing clarity of the emulsion without refractive index matching of the sample fluid and the one or more fluid layers 420'; inducing one or more reactions upon processing the emulsion with a set of operations 430'; detecting signals emitted from a subset of droplets containing target material from the sample fluid 440'; and performing a quantification operation with the subset of droplets 450'.

Generating the set of droplets and generating the emulsion in steps 410 and 420', respectively, can be performed according to methods (e.g., method 300, method 300') described above and/or according to other suitable methods.

Furthermore, as described above, in embodiments, the sample fluid can include target material (e.g., nucleic acids), and in specific examples, the droplets can be generated from a sample fluid with a PCR master mix containing polymerase, dNTPs, template DNA molecules, primers, probes and/or a solute (e.g., sugar or salt component). As such, generation of droplets according to the method 400' can produce an emulsion having suitable clarity, where some, but not all droplets generated contain the target material. Inducing one or more reactions upon processing the emulsion in step 430' can thus include performing one or more steps associated with amplification and detection of nucleic acids (e.g., thermocycling, incubating, mixing, etc.) within the collecting container.

Post-reaction, the method 400 can include detecting signals emitted from a subset of droplets containing target material from the sample fluid 440', where positive signals are associated with presence of target material captured within individual droplets of the subset of droplets. The detected signals are preferably optically-detectable (e.g., using an optical detection subsystem, using an imaging subsystem, etc.), where embodiments, variations, and examples of an optical detection subsystem are described in in PCT Application PCT/CN2019/093241 filed 27 Jun. 2019, incorporated by reference above; however, in variations, the signals can be detectable in another suitable manner by other suitable apparatus.

As shown in FIG. 7D, the method 400' includes performing a quantification operation with the subset of droplets in step 450'. In particular, performing the quantification operation can be implemented in a manner such that only the subset of droplets that positively emit signal associated with target material are counted according to the quantification operation, without counting of droplets that do not positively emit signal. As such, in contrast to other droplet-based approaches, the method 400' can omit counting of droplets that do not positively emit signal associated with the target material, as shown in FIG. 7, thus providing an improved and more efficient process with rapid generation of results.

In specific applications, above-described methods for droplet digital PCR can be used for or adapted for (e.g., in relation to analytes other than nucleic acids and reactions other than PCR) one or more of: enumeration of protein or peptide molecules (e.g., by proximity ligation assays, etc.); sequencing applications (e.g., single molecule sequencing applications); monitoring or detection of products (e.g., proteins, chemicals) released from single cells (e.g., interleukin released from immune cells); monitoring cell survival and/or division for single cells; monitoring or detection of enzymatic reactions involving single cells; antibiotic resistance screening for single bacteria; enumeration of pathogens in a sample (e.g., in relation to infections, sepsis, in relation to environmental and food samples, etc.); enumeration of heterogeneous cell populations in a sample; enumeration of individual cells or viral particles (e.g., by encapsulating cells in droplets with species-specific antibodies coupled with enzymes that react with substrate components in the droplet to produce signals, etc.); monitoring of viral infections of a single host cell; liquid biopsies and companion diagnostics; prenatal diagnosis of genetic disorders (e.g., aneuploidy, genetically inherited diseases) such as with cell-free nucleic acids, fetal cells, or samples containing mixtures of fetal and maternal cells based upon generated counts and subsequent characterization of target nucleic acids; detection of cancer forms from various biological samples (e.g., from cell-free nucleic acids, tissue biopsies, biological fluids, faeces) based upon generated counts and subsequent characterization of target nucleic acids; detection and/or monitoring of minimal residual diseases; monitoring responses to therapies; detection or prediction of rejection events of transplanted organs; other diagnostics associated with other health conditions; other characterizations of statuses of other organisms; and other suitable applications.

3.4 Emulsion Generation—Additional Applications

Variations of the method 300 can additionally or alternatively include other steps involving adjustments to the temperature(s) of emulsions generated, where the emulsions are stable across temperature ranges in use. In terms of stability, the components of the disperse phase and the continuous phase of the emulsion can be configured such that the film(s) about each droplet of the disperse phase are stable and do not break or result in droplet coalescence across temperature ranges in use. In particular, temperature adjustments can be associated with thermocycling (e.g., for amplification processes), temperatures for cell culture applications, temperatures storage (e.g., at refrigerated temperatures, at ambient temperatures), and/or other temperatures used for applications in other fields (e.g., pharmaceutical applications, food production applications, etc.). In a specific example, the emulsion generated is stable for across material storage and thermocycling applications, for instance, between 4 C and 95 C (e.g., for 20-30 minutes).

Additionally or alternatively, in some variations, the method 300 can include steps associated with performance of multi-step reactions or analyses. For instance, in relation to generating emulsions, the method 300 can include passing droplets of the dispersed phase through multiple layers of a set of fluid layers, where each layer includes components associated with a reaction (e.g., tagging with a moiety, generation of a product, etc.). In one such example, a components of a droplet can "pick up", bind to, or otherwise react with content of each fluid layer encountered, to perform multi-step reactions.

In another variation, the method 300 can additionally or alternatively include steps for receiving additional fluids into the collecting container after an initial emulsion is generated. For instance, after an initial emulsion is generated and/or a product is generated from a reaction associated with components of the emulsion, the method 300 can include receiving one or more additional material components into the collecting container (e.g., through an opening, through a valved connection into the collecting container, etc.) where the additional material components can be configured to react with or interact with the emulsion in some manner for a downstream application.

However, the method 300 can additionally or alternatively include other steps for generating, processing, and/or using emulsions having suitable clarity for at least one stage of processing.

3.5 Method—Specific Example for Antimicrobial Susceptibility Testing

In specific example applications, clear emulsions generated by the method 300 can be used for antimicrobial susceptibility testing, where a sample fluid can include a fluorescent compound reactive with target material of the sample fluid. The method can then include performing fluorescent imaging of the emulsion generated from the sample fluid, within the collecting container, and processing readout signals from individual droplets of the emulsion within the collecting container. In more detail, in a specific example, a solution containing bacteria and an antibiotic for susceptibility testing can be combined with a fluorescent growth indicator (e.g., resazurin) and/or a live-dead staining component. The solution can then be processed to generate droplets (e.g., by centrifugation through an example of the system 100 described above) the droplets. In this example, the amount of bacteria used is configured to be smaller than the number of droplets generated, such that each droplet contains one or zero bacterium units, with antibiotic components. In the example, antibiotic efficacy is assessed by imaging droplets, as droplets containing live/growing and dead bacterium units will fluoresce according to the live-dead stain. Imaging of droplets is thus enabled due to the transparency of the emulsion (e.g., having greater than 80% optical transmittance of light, having another suitable level of light transmittance, etc.), which enables reading of fluorescence of individual droplets throughout the tube (e.g., using confocal imaging, using light sheet imaging). Furthermore, due to the small volume of each droplet of the disperse phase of the emulsion, signals can be observed after only a few cell replication cycles. This reduces turn-around time for results from a few days of typical plate-based culture to a few hours or less. The digital read-out also enables one to monitor heterogeneous response to antibiotic of the microbial community in the sample.

Alternative to fluorescent monitoring of growth associated dyes in the example described above, an increase in number of cells within a droplet and/or generation of reaction products can cause the droplet to have different light scattering properties. As such, droplet turbidity can be measured quantitatively by a turbidimeter or spectrophotometer, or even by visual observation.

The method 300 can, however, be applied to other specific applications in relation to processing and/or analyzing sample emulsions.

4. Conclusions

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or, if applicable, portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A method comprising:
performing a digital analysis of a sample distributed across a set of partitions,
wherein performing the digital analysis comprises imaging a set of cross-sections of a closed container containing the set of partitions, wherein the set of partitions has a number greater than 1 million partitions, and wherein the digital analysis is performed within three minutes.

2. The method of claim 1, wherein the digital analysis is performed within two minutes.

3. The method of claim 1, wherein imaging the set of cross-sections of the closed container comprises performing readout of signals from contents of partitions represented in each of the set of cross-sections.

4. The method of claim 3, wherein the signals comprise fluorescent signals from labelled target analytes of the sample.

5. The method of claim 1, wherein the set of partitions comprises a set of droplets of an emulsion generated from the sample, wherein clarity of the emulsion is produced without refractive index matching of the sample and other materials of the emulsion.

6. The method of claim 5, wherein each of the set of droplets has a characteristic diameter from 10 microns to 100 microns.

7. The method of claim 5, wherein the set of droplets is characterized by less than 5% occupancy by target analytes of the sample.

8. The method of claim 1, wherein the closed container has a volume from 10 to 100 microliters.

9. The method of claim 1, wherein performing the digital analysis comprises analyzing up to 1.4 million nucleic acid molecules of the sample without application of Poisson statistics to correct for partitioning error.

10. The method of claim 1, wherein the sample comprises a nucleic acid mixture combined with a solution for polymerase chain reaction (PCR) and a density medium.

11. The method of claim 10, wherein the nucleic acid mixture comprises cell-free nucleic acids.

12. The method of claim 1, wherein the sample comprises material derived from fetal cells and maternal cells, and wherein performing the digital analysis further comprises performing prenatal detection of aneuploidy.

13. The method of claim 1, wherein the sample comprises a protein solution.

14. The method of claim 1, wherein imaging the closed container comprises performing a 3D scanning technique.

15. The method of claim 1, wherein imaging the closed container comprises performing a planar imaging technique.

16. A method comprising:
performing a digital analysis of a set of droplets generated from a sample and retained at equilibrium positions within a continuous fluid layer within a closed container,
wherein performing the digital analysis comprises scanning one or more cross-sections of the closed container, wherein the set of droplets has a number greater than 1 million droplets, and wherein the digital analysis is performed within three minutes.

17. The method of claim 16, wherein each of the set of droplets has a characteristic diameter greater than 1 micron.

18. The method of claim 16, wherein scanning one or more cross-sections comprises performing at least one of a 3D scanning technique and a planar imaging technique.

19. The method of claim 16, wherein:
the sample comprises a first aqueous solution comprising target nucleic acids, a mixture for polymerase chain reaction (PCR), and a density medium,
the continuous fluid layer comprises a second aqueous solution, and
the set of droplets generated from the sample are individually isolated and separated from the second aqueous solution by a non-aqueous solution.

20. The method of claim 19, wherein performing the digital analysis further comprises performing a temperature adjustment operation on the set of droplets at the equilibrium positions, wherein the set of droplets is thermally stable during the temperature adjustment operation.

21. A method comprising:
performing a digital analysis of a set of droplets generated from a sample and retained at equilibrium positions within a continuous fluid layer within a closed container,
wherein performing the digital analysis comprises scanning a set of cross-sections of the closed container,
wherein the set of droplets comprises 3.5 million droplets,
wherein the digital analysis is performed within three minutes, and
wherein performing the digital analysis comprises performing prenatal detection of a genetic disorder.

* * * * *